United States Patent
Goldman et al.

(10) Patent No.: US 12,282,031 B2
(45) Date of Patent: Apr. 22, 2025

(54) MASS SPECTROMETRIC DETERMINATION OF TERT-BUTYLDIMETHYLSILYL DERIVATIZED METHYLMALONIC ACID

(71) Applicant: Quest Diagnostics Investments Incorporated, Wilmington, DE (US)

(72) Inventors: Scott M. Goldman, Laguna Niguel, CA (US); Julie A. Neidich, Ladera Ranch, CA (US); Denise Salazar, Altadena, CA (US); Thomas Lynn, Temecula, CA (US)

(73) Assignee: Quest Diagnostics Investments, LLC

( * ) Notice: Subject to any disclaimer, the term of this patent is extended or adjusted under 35 U.S.C. 154(b) by 312 days.

(21) Appl. No.: 17/096,475

(22) Filed: Nov. 12, 2020

(65) Prior Publication Data

US 2021/0132086 A1     May 6, 2021

Related U.S. Application Data

(63) Continuation of application No. 13/156,307, filed on Jun. 8, 2011, now Pat. No. 10,837,972.

(60) Provisional application No. 61/353,172, filed on Jun. 9, 2010.

(51) Int. Cl.
    *G01N 33/82*    (2006.01)
    *H01J 49/00*    (2006.01)
    *G01N 30/72*    (2006.01)

(52) U.S. Cl.
    CPC ............. *G01N 33/82* (2013.01); *G01N 30/72* (2013.01); *G01N 2560/00* (2013.01); *H01J 49/00* (2013.01); *Y10T 436/201666* (2015.01)

(58) Field of Classification Search
    CPC ................................. G01N 33/82; H01J 49/00
    USPC ................................................ 436/129, 173
    See application file for complete search history.

(56) References Cited

U.S. PATENT DOCUMENTS

| | | | |
|---|---|---|---|
| 2,768,301 A * | 10/1956 | Bennett | H01J 49/36 250/283 |
| 2,978,580 A * | 4/1961 | Von Ardenne | H01J 49/123 313/7 |
| 3,860,848 A * | 1/1975 | Knof | H01J 49/147 313/231.01 |
| 4,940,658 A | 7/1990 | Allen et al. | |
| 5,055,677 A * | 10/1991 | Amirav | H01J 49/00 250/288 |
| 5,438,017 A | 8/1995 | Allen et al. | |
| 5,457,055 A | 10/1995 | Allen et al. | |
| 5,559,038 A | 9/1996 | Kolhouse et al. | |
| 5,772,874 A | 6/1998 | Quinn et al. | |
| 5,795,469 A | 8/1998 | Quinn et al. | |
| 5,800,979 A | 9/1998 | Kolhouse et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koester | |
| 6,692,971 B2 | 2/2004 | Shushan et al. | |
| 6,808,933 B1 * | 10/2004 | Prest | G01N 30/62 210/656 |
| 7,993,931 B1 | 8/2011 | Chen | |
| 10,837,972 B2 * | 11/2020 | Goldman | G01N 33/82 |
| 2002/0019056 A1 | 2/2002 | Shushan et al. | |
| 2005/0165560 A1 | 7/2005 | Kushnir et al. | |
| 2008/0199960 A1 * | 8/2008 | Juliano | C12N 15/111 435/325 |
| 2008/0296486 A1 * | 12/2008 | Blanksby | H01J 49/0045 250/288 |
| 2010/0084549 A1 * | 4/2010 | Ermakov | H01J 49/4245 250/293 |
| 2010/0297774 A1 * | 11/2010 | Green | G01N 33/03 436/56 |
| 2010/0304492 A1 * | 12/2010 | Melechco Carvalho | G01N 33/82 436/63 |
| 2010/0320373 A1 * | 12/2010 | Appelblad | B01D 15/364 250/282 |

FOREIGN PATENT DOCUMENTS

| | | | | |
|---|---|---|---|---|
| WO | 2008052299 A2 | 5/2008 | | |
| WO | WO-2008101736 A1 * | 8/2008 | ........... | B01D 15/364 |

OTHER PUBLICATIONS

Hempen, C. et al., Analytical and Bioanalytical Chemistry 2008, 391, 263-270.*
Magera, M. L. et al., Clinica Chimica Acta 2001, 306, 35-41. (Year: 2001).*
Willoughby, R. C. et al, Analytical Chemistry 1984, 56, 2626+2631. (Year: 1984).*
Baty, J. D. et al, Biomedical CHromatography 1985, 12, 565-569. (Year: 1985).*
De Wit, J. S. M. et al, Analytical Chemistry 1987, 59, 2400-2404. (Year: 1987).*
Winkler, P. D. et al, Analytical Chemistry 1988, 60, 489-493. (Year: 1988).*
Arpino, P., Fresenius Journal of Analytical Chemistry 1990, 337, 667-685. (Year: 1990).*
Hsu, C. S. et al, Energy & Fuels 1991, 5, 395-398. (Year: 1991).*

(Continued)

*Primary Examiner* — Arlen Soderquist

(74) *Attorney, Agent, or Firm* — Quest Diagnostics, Inc.

(57) ABSTRACT

The invention relates to the detection of methylmalonic acid (MMA). In a particular aspect, the invention relates to methods for detecting derivatized methylmalonic acid (MMA) by mass spectrometry.

5 Claims, 11 Drawing Sheets

(56) References Cited

OTHER PUBLICATIONS

Qian, K. et al, Analytical Chemistry 1992, 64, 2327-2333. (Year: 1992).*
Hsu, C. S. et al, Journal of High Resolution Chromatography 1994, 17, 271-276. (Year: 1994).*
Kientz, C. E. et al, Analytical Chemistry 1996, 68, 675-681. (Year: 1996).*
Cappiello, A. et al, Mass Spectrometry Reviews 2005, 24, 978-989. (Year: 2005).*
Cappiello, A. et al, Analytical Chemistry 2007, 79, 5364-5372. (Year: 2007).*
Cappiello, A. et al, Analytical Chemistry 2008, 80, 9343-9348. (Year: 2009).*
Erro, J et al, Journal of Agricultural and Food Chemistry 2009, 57, 4004-4010. (Year: 2009).*
Mills, G. A. et al, Biomedical and Environmental Mass Spectrometry 1988, 16, 259-261. (Year: 1988).*
Bourcier, S. et al, European Journal of Mass Spectrometry 2003, 9, 351-360. (Year: 2003).*
Electron volt definition downloaded Sep. 27, 2024 from https://www.britannica.com/science/electron-volt. (Year: 2024).*
Aguera A., et al., "One-Year Routine Application of a New Method Based On Liquid Chromatography-Tandem Mass Spectrometry to the Analysis of 16 Multiclass Pesticides in Vegetable Samples," Journal of Chromatography A, Aug. 2004, vol. 1045 (1-2), pp. 125-135.
"Analytical Detection Limit Guidance & Laboratory Guide for Determining Method Detection Limits" PUBL-TS-056-96 published Apr. 1996 by the Wisconsin Department of Natural Resources Laboratory Certification Program, 33 pages.
Appelblad P., et al., "Mass Spectrometric Detection of Homocysteine, Methylmalonic Acid and Succinic Acid using HILIC on a Zwitterionic Stationary Phase," LC-GC Europe, 2005, vol. 18, pp. 47.
Ardrey R.E., "Liquid Chromatography-Mass Spectrometry: An Introduction" Chapters 3 and 5, pp. 33-74 and 129-234, 2003, John Wiley & Sons, Ltd.
Armbruster D. A., et al., "Limit of Blank, Limit Of Detection And Limit Of Quantitation," The Clinical Biochemist Reviews, 2008, vol. 29 (1), pp. S49-S52.
Armbruster D.A., et al., "Limit of Detection (LOD)/limit of Quantitation (LOQ): Comparison Of The Empirical And The Statistical Methods Exemplified With GC-MS Assays of Abused Drugs," Clinical Chemistry, 1994, vol. 40 (7), pp. 1233-1238.
Bader M., et al., "The use of gas chromatography-mass spectrometry" in The MAK-Collection Part IV: Biomonitoring Methods, vol. 10, 3-51, WILEY-VCH Verlag Gmbh & Co. KGaA, Weinheim.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Bates-Dubrow L., et al., "Analysis of Urinary Organic Acids by GC Tandem Mass Spectrometry for the Accurate Diagnosis of Inborn Errors of Metabolism," ASMS Conference, 2010, pp. 2.
Blom H.J., et al., "A Simple High-throughput Method for the Determination of Plasma Methylmalonic Acid by Liquid Chromatography-tandem Mass Spectrometry," Clinical Chemistry and Laboratory Medicine, 2007, vol. 45 (5), pp. 645-650.
Busch M., et al., "Validated Capillary Gas Chromatographic-Mass Spectrometric Assay to Determine 2-Methylcitric Acid I and II Levels in Human Serum by using a Pulsed Splitless Injection Procedure," Journal of Chromatography B, 2002, vol. 775 (2), pp. 215-223.
Cappiello A., et al., "A Simple Approach for Coupling Liquid Chromatography and Electron Ionization Mass Spectrometry," Journal of the American Society for Mass Spectrometry, 2002, vol. 13 (3), pp. 265-273.
Cappiello A., et al., "New Liquid Chromatography/electron Ionization Mass Spectrometry Methods in Water Analysis," Annali di Chimica, 2002, vol. 92 (7-8), pp. 623-636.
Carvalho V.M., et al., "Determination of Serum Methylmalonic Acid by Alkylative Extraction and Liquid Chromatography Coupled to Tandem Mass Spectrometry," Analytical Biochemistry, 2008, vol. 381 (1), pp. 67-73.
Cervera M.I., et al., "Multi-Residue Determination of 130 Multiclass Pesticides in Fruits and Vegetables by Gas Chromatography Coupled to Triple Quadrupole Tandem Mass Spectrometry," Analytical and Bioanalytical Chemistry, 2010, vol. 397, pp. 2873-2891.
Chen J., et al., "Quantitation of Methylmalonic Acid in Serum or Plasma Using Isotope Dilution-Selected Ion Gas Chromatography-Mass Spectrometry," Clinical Applications of Mass Spectrometry, 2010, vol. 603, pp. 365-370.
Child-Specific Exposure Factors Handbook, Chapter 5, pp. 5i-4-42, Sep. 2008.
Christensson B., et al., "Mass Spectrometric Quantitation of Muramic Acid, A Bacterial Cell Wall Component, in Septic Synovial Fluids," Arthritis & Rheumatism, 1989, vol. 32 (10), pp. 1268-1272.
Courant F., et al., "Assessment of Circulating Sex Steroid Levels in Prepubertal and Pubertal Boys and Girls by a Novel Ultrasensitive Gas Chromatography-Tandem Mass Spectrometry Method," The Journal of Clinical Endocrinology & Metabolism, Jan. 2010, vol. 95 (1), pp. 82-92.
De Jong A.P.J.M., et al., "Gas Chromatography Mass Spectrometry of t-Butyldimethylsilyl Derivatives of Organic Acids," Biomedical Mass Spectrometry, 1980, vol. 7 (8), pp. 359-364.
Driskell W. J., et al., "Quantitation of Organophosphorus Nerve Agent Metabolites in Human Urine Using Isotope Dilution Gas Chromatography-Tandem Mass Spectrometry," Journal of Analytical Toxicology, 2002, vol. 26 (1), pp. 6-10.
Edlund A., et al., "A Microscale Technique for Gas Chromatography-Mass Spectrometry Measurements of Picogram Amounts of Indole-3-Acetic Acid in Plant Tissues," Plant physiology, 1995, vol. 108 (3), pp. 1043-1047.
Fasching C., et al., "Clinical Applications of Mass Spectrometry", Methods in Molecular Biology, Chapter 36, p. 371.
Fiehn O., et al., "Mass Spectrometry: Quantitation" In: D Ganten and K Ruckpaul (Editors): "Encyclopedic Reference of Genomics and Proteomics in Molecular Medicine", Springer, 2006, pp. 1030-1034.
Fox A., et al., "Gas Chromatography-Tandem Mass Spectrometry for Trace Detection of Muramic Acid, A Peptidoglycan Chemical Marker, in Organic Dust," Journal of Microbiological Methods, 1995, vol. 22 (1), pp. 11-26.
Fox A., et al., "Monitoring of Bacterial Sugars and Hydroxy Fatty Acids in Dust From Air Conditioners by Gas Chromatography-Mass Spectrometry," Applied and Environmental Microbiology, 1993, vol. 59 (12), pp. 4254-4260.
Fredriksson S.A., et al., "Trace Determination of Alkyl Methylphosphonic Acids in Environmental and Biological Samples Using Gas Chromatography/Negative-Ion Chemical Ionization Mass Spectrometry and Tandem Mass Spectrometry," Journal of Mass Spectrometry, Aug. 1995, vol. 30 (8), pp. 1133-1143.
Gaskell S.J., et al., "Trace Analysis by Gas Chromatography/Mass Spectrometry (GC/MS) using A Tandem Double-Focusing/Quadrupole Instrument," Biomedical Mass Spectrometry, 1985, vol. 12 (3), pp. 139-141.
Hagen T., et al., "A GC/MS/MS Screening Method for Multiple Organic Acidemias from Urine Specimens," Clinica Chimica Atca, 1999, vol. 283 (1-2), pp. 77-88.
Hasegawa Y., et al., "Prenatal Diagnosis for Organic Acid Disorders Using Two Mass Spectrometric Methods, Gas Chromatography Mass Spectrometry and Tandem Mass Spectrometry," Journal of Chromatography B, 2005, vol. 823, 13-17.
Hernando M. D., et al., "Comparative Study of Analytical Methods Involving Gas Chromatography-Mass Spectrometry After Derivatization and Gas Chromatography-tandem Mass Spectrometry for the Determination of Selected Endocrine Disrupting Compounds in Wastewaters," Journal of Chromatography, Aug. 2004, vol. 1047(1), pp. 129-135.

(56) References Cited

OTHER PUBLICATIONS

International Search Report for Application No. PCT/US2011/039652, mailed on Sep. 28, 2011, 2 Pages.

Jessome L.L., et al., "Ion Suppression: A Major Concern in Mass Spectrometry," LCGC North America, May 2006, vol. 24 (5), pp. 498-510.

Johnson J.V., et al., "Tandem Mass Spectrometry for Trace Analysis," Analytical Chemistry, 1985, vol. 57 (7), pp. 758A-760A, 762A, 764A,766A and 768A.

Johnson J.V., et al., "Tandem-in-Space and Tandem-in-Time Mass Spectrometry: Triple Quadrupoles and Quadrupole Ion Traps," Analytical Chemistry, 1990, vol. 62 (20), pp. 2162-2172.

Kawana S., et al., "Improvement of Sample Throughput Using Fast Gas Chromatography Mass-Spectrometry for Biochemical Diagnosis of Organic Acid Disorders," Clinica Chimica Acta, 2008, vol. 392, pp. 34-40.

Kelly C., "Analysis of Steroids in Environmental Water Samples Using Solid-Phase Extraction and Ion-Trap Gas Chromatography-Mass Spectrometry and Gas Chromatography-Tandem Mass Spectrometry," Journal of Chromatography A, Mar. 2000, vol. 872 (1-2), pp. 309-314.

Kharbouche H., et al., "Development and Validation of a Gas Chromatography-Negative Chemical Ionization Tandem Mass Spectrometry Method for the Determination of Ethyl Glucuronide in Hair and Its Application to Forensic Toxicology," Journal of Chromatography B, 2009, vol. 877 (23), pp. 2337-2343.

Kushnir M.M., et al., "Analysis of Dicarboxylic Acids by Tandem Mass Spectrometry. High-Throughout Quantitative Measurement of Methylmalonic Acid in Serum, Plasma and Urine," Clinical Chemistry, 2001, vol. 47 (11), pp. 1993-2002.

Kushnir M.M., et al., "Assessing Analytical Specificity in Quantitative Analysis Using Tandem Mass Spectrometry," Clinical Biochemistry, Apr. 2005, vol. 38 (4), pp. 319-327.

Kushnir M.M., et al., "Development and Performance Evaluation of a Tandem Mass Spectrometry Assay for 4 Adrenal Steroids," Clinical Chemistry, 2006, vol. 52 (8), pp. 1559-1567.

Kushnir M.M., et al., "Optimization and Performance of a Rapid Gas Chromatography-Mass Spectrometry Analysis for Methylmalonic Acid Determination in Serum and Plasma," Journal of Chromatography B, 2000, vol. 741 (2), pp. 231-241.

La Marca G., et al., "Rapid 2nd-tier Test for Measurement of 3-OH-propionic and Methylmalonic Acids on Dried Blood Spots: Reducing the False-positive Rate for Propionylcarnitine During Expanded Newborn Screening by Liquid Chromatography-tandem Mass Spectrometry," Clinical Chemistry, 2007, vol. 53 (7), pp. 1364-1369.

Lakso H., et al., "Quantification of Methylmalonic Acid in Human Plasma with Hydrophilic Interaction Liquid Chromatography Separation and Mass Spectrometric Detection," Clinical Chemistry, 2008, vol. 54 (12), pp. 2028-2035.

Luo X., et al., "Methylmalonic Acid in Amniotic Fluid and Maternal Urine as a Marker for Neural Tube Defects," Journal of Huazhong University of Science and Technology, 2004, vol. 24 (2), pp. 166-169.

Magera M.J., et al., "Methylmalonic Acid Measured in Plasma and Urine by Stable-Isotope Dilution and Electrospray Tandem Mass Spectrometry," Clinical Chemistry, 2000, vol. 46 (11), pp. 1804-1810.

Marcell P.D., et al., "Quantitation of Methylmalonic Acid and Other Dicarboxylic Acids in Normal Serum and Urine Using Capillary Gas Chromatography-Mass Spectrometry," Analytical Chemistry, 1985, vol. 150 (1), pp. 58-66.

Marcos J., et al., "Fast Screening of Anabolic Steroids and Other Banned Doping Substances in Human Urine by Gas Chromatography/Tandem Mass Spectrometry," Journal of Mass Spectrometry, Oct. 2002, vol. 37 (10), pp. 1059-1073.

Mccann M.T., et al., "Methylmalonic Acid Quantification by Stable Isotope Dilution Gas Chromatography-Mass Spectrometry from Filter Paper Urine Samples," Clinical Chemistry, 1996, vol. 42 (6 Pt 1), pp. 910-914.

Mcghie T.K., "Analysis of Serum Methylmalonic Acid for the Determination of Cobalt Deficiency in Cattle," Journal of Chromatography, 1991, vol. 566 (1), pp. 215-222.

Mcghie T.K., et al., "Quantitative Analysis of Hexythiazox by Direct Insertion Probe Mass Specytrometry," Biomedical and Environmental Mass Spectrometry, 1990, vol. 19 (4), pp. 267-272.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Moritz T., et al., "Comparison Between High-Resolution Selected Ion Monitoring, Selected Reaction Monitoring, and Four-Sector Tandem Mass Spectrometry in Quantitative Analysis of Gibberellins in Milligram Amounts of Plant Tissue," Analytical Chemistry, 1995, vol. 67 (10), pp. 1711-1716.

National Center for Biotechnology Information. PubChem Compound Database; CID=441038, https://pubchem.ncbi.nlm.nih.gov/compound/441038 (accessed Oct. 23, 2015).

Non-Final Office Action mailed Jan. 22, 2016 for U.S. Appl. No. 14/063,956, filed Oct. 25, 2013.

Norris A.J., et al., "Analysis of Enzyme Kinetics using Electrospray-Ionization Mass Spectrometryand multiple Reaction Monitoring: Fucosyltransferase V," Biochemistry, 2001, vol. 40, pp. 3774-3779.

Ohie T., et al., "Gas Chromatography-Mass Spectrometry with Tert.-Butyldimethylsilyl Derivation: Use of the Simplified Sample Preparations and the Automated Data System to Screen for Organic Acidemias," Journal of Chromatography B, 2000, vol. 746 (1), pp. 63-73.

Park Y.J., et al., "Gas Chromatographic Organic Acid Profiling Analysis of Brandies and Whiskeys for Pattern Recognition Analysis," Journal of Agricultural and Food Chemistry, 1999, vol. 47 (6), pp. 2322-2326.

Peters H., et al., "A Knock-out Mouse Model for Methylmalonic Aciduria Resulting in Neonatal Lethality," Journal of Biological Chemistry, 2003, vol. 278 (52), pp. 52909-52913.

Pitt J.J., et al., "Comprehensive Screening of Urine Samples for Inborn Errors of Metabolism by Electospray Tandem Mass Spectrometry," Clinical Chemistry, 2002, vol. 48 (11), pp. 1970-1980.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Purevsuren J., et al., "Urinary Organic Metabolite Screening of Children with Influenza-Associated Encephalopathy for Inborn Errors of Metabolism Using GC/MS," Brain and Development, 2008, vol. 30 (8), pp. 520-526.

Qu L.J., et al., "Rapid Determination of Organophosphorous Pesticides in Leeks by Gas Chromatography-Triple Quadrupole Mass Spectrometry," Food Chemistry, Sep. 2010, vol. 122 (1), pp. 327-332.

Rashed M.S., et al., "Screening Blood Spots for Inborn Errors of Metabolism by Electrospray Tandem Mass Spectrometry With a Microplate Batch Process And a Computer Algorithm for Automated Flagging Of Abnormal Profiles," Clinical Chemistry, Jul. 1997, vol. 43 (7), pp. 1129-1141.

Rasmussen K., "Solid-Phase Sample Extraction for Rapid Determination of Methylmalonic Acid in Serum and Urine by a Stable-Isotope-Dilution Method," Clinical Chemistry, 1989, vol. 35 (2), pp. 260-264.

Regueiro J., et al., "Trace Analysis of Parabens, Triclosan and Related Chlorophenols in Water by Headspace Solid-phase Microextraction With in Situ Derivatization and Gas Chromatography-Tandem Mass Spectrometry," Journal of Chromatography A, Jun. 2009, vol. 1216 (23), pp. 4693-4702.

Rifai N., et al., "Determination of Serum Physiological Concentration of Methylmalonic Acid By Gas Chromatography-Mass Spectrometry with Selected Ion Monitoring," Annals of Clinical Biochemistry, 1998, vol. 35 (Pt 5), pp. 633-636.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Schmedes A., et al., "Analysis of Methylmalonic Acid in Plasma by Liquid Chromatography-Tandem Mass Spectrometry," Clinical Chemistry, 2006, vol. 52 (4), pp. 754-757.

(56) References Cited

OTHER PUBLICATIONS

Schummer C., et al., "Comparison of MTBSTFA and BSTFA in Derivatization Reactions of Polar Compounds Prior to GC/MS Analysis," Talanta, 2009, vol. 77 (4), pp. 1473-1482.
Shigematsu Y., et al., "Useful Second-Tier Tests in Expanded Newborn Screening of Isovaleric Acidemia and Methylmalonic Aciduria," Journal of Inherited Metabolic Disease, 2010, vol. 33 (Supplement 2), pp. S283-S288.
Song Y.Z., et al., "Selective Screening for Inborn Errors of Metabolism and Secondary Methylmalonic Aciduria in Pregnancyat High Risk District of Neural Tube Defects: A Human Metabolome Study by GC-MS in China," Clinical Biochemistry, 2008, vol. 41 (7-8), pp. 616-620.
Specker B.L., et al., "Urinary Methylmalonic Acid Excretion in Infants Fed Formula or Human Milk," The American Journal of Clinical Nutrition, 1990, vol. 51 (2), pp. 209-211.
Stabler S.P., et al. , "Assay of Methylmalonic Acid in the Serum of Patients with Cobalamin Deficiency Using Capillary Gas Chromatography-Mass Spectrometry," Journal of Clinical Investigation, 1986, vol. 77 (5), pp. 1606-1612.
Stabler S.P., et al., "Failure to Detect Beta-leucine in Human Blood or Leucine 2,3-aminomutase in Rat Liver Using Capillary Gas Cchromatography-mass Spectrometry," Journal of Biological Chemistry, 1988, vol. 263 (12), pp. 5581-5588.
Straczek J., et al., "Quantification of Methylmalonic Acid in Serum Measured by Capillary Gas Chromatography-Mass Spectrometry as Tert.-Butyldimethylsilyl Derivatives," Journal of Chromatography, 1993, vol. 620 (1), pp. 1-7.
Thurman E.M., et al., "Chromatographic-Mass Spectrometric Food Analysis for Trace Determination of Pesticide Residues," Amadeo R., et al., eds., Elsevier, 2005, Chapter 8, pp. 369-401.
Tsikas D., "Application of Gas Chromatography-Mass Spectrometry and Gas Chromatography-tandem Mass Spectrometry to Assess in Vivo Synthesis of Prostaglandins, Thromboxane, Leukotrienes, Isoprostanes and Related Compounds in Humans," Journal of Chromatography B: Biomedical Sciences and Applications, Oct. 1998, vol. 717(1-2), pp. 201-245.
Tuchman M., et al., "Screening Urine of 3-Week-Old Newborns: Transient Methylmalonic and Hydroxyphenyllactic Aciduria," Biochemical Medicine and Metabolic Biology, 1992, vol. 48 (1), pp. 64-68.
Ueland P.M., et al., "Quantitative Profiling Of Folate and One-Carbon Metabolism in Large-Scale Epidemiological Studies by Mass Spectrometry," Clinical Chemistry and Laboratory Medicine, 2007, vol. 45 (12), pp. 1737-1745.
Vandenberghe Y., et al., "Effect of Folate Supplementation on Clinical Chemistry and Hematologic Changes Related to Bidisomide Administration in the Rat," Drug and Chemical Toxicology, 1995, vol. 18 (4), pp. 235-270.
Verma, K.K., et al, "On-line Solid-Phase Extraction-Gas Chromatography-Ion Trap Tandem Mass Spectrometric Detection for the Nanogram Per Liter Analysis of Trace Pollutants in Aqueous Samples," Chromatographia, Apr. 1997, vol. 44(7-8), pp. 372-380.
Volmer D.A., et al., "Study of 4-Quinolone Antibiotics in Biological Samples by Short-Column Liquid Chromatography Coupled With Electrospray Ionization Tandem Mass Spectrometry," Analytical Chemistry, 1997, vol. 69 (20), pp. 4143-4155.
Walorczyk S., "Development of a Multi-Residue Screening Method for the Determination of Pesticides in Cereals and Dry Animal Feed Using Gas Chromatography-Triple Quadrupole Tandem Mass Spectrometry," Journal of Chromatography A, Aug. 2007, vol. 1165 (1-2), pp. 200-212.
Walorczyk S., et al., "Development and Validation of a Multi-Residue Method for the Determination of Pesticides in Honeybees Using Acetonitrile-Based Extraction and Gas Chromatography-Tandem Quadrupole Mass Spectrometry," Journal of Chromatography A, Sep. 2009, vol. 1216 (37), pp. 6522-6531.
Wasant P., "Neonatal Screening in the 21st Century," Southeast Asian Journal of Tropical Medicine and Public Health, 1998, vol. 30, pp. 160-165.
Windelberg A., et al., "Automated Assay for the Determination of Methylmalonic Acid, Total Homocysteine, and Related Amino Acids in Human Serum or Plasma By Means of Methylchloroformate Derivatization and Gas Chromatography-Mass Spectrometry," Clinical Chemistry, 2005, vol. 51 (11), pp. 2103-2109.
Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.
Written Opinion for Application No. PCT/US2011/039652, mailed on Sep. 28, 2011, 6 Pages.
Yazdanpanah M., et al., "An Improved Assay for Plasma Methylmalonic Acid Using Chemical Ionization Gas Chromatography Mass Spectrometry," Clinical Biochemistry, 2003, vol. 36 (8), pp. 617-620.
Young P.B., et al., "Sensitive Gas Chromatographic-High Resolution Mass Spectrometric Method for the Determination of Methylmalonic Acid in Bovine Plasma," Analyst, 1995, vol. 120 (8), pp. 2199-2201.
Zinn A.B., et al., "The Stable Isotope Dilution Method for Measurement of Methylmalonic Acid: A Highly Accurate Approach to the Prenatal Diagnosis of Methylmalonic Acidemia," Pediatric Research, 1982, vol. 16 (9), pp. 740-745.
Final Office Action mailed Dec. 10, 2015 for U.S. Appl. No. 13/156,307, filed Jun. 8, 2011.
Final Office Action mailed Oct. 16, 2014 for U.S. Appl. No. 13/156,307, filed Jun. 8, 2011.
Final Office Action mailed Jan. 31, 2018 for U.S. Appl. No. 13/156,307, filed Jun. 8, 2011.
Non-Final Office Action mailed Oct. 7, 2013 for U.S. Appl. No. 13/156,307, filed Jun. 8, 2011.
Non-Final Office Action mailed Apr. 20, 2017 for U.S. Appl. No. 13/156,307, filed Jun. 8, 2011.
Non-Final Office Action mailed Sep. 21, 2018 for U.S. Appl. No. 13/156,307, filed Jun. 8, 2011.
Non-Final Office Action mailed May 22, 2015 for U.S. Appl. No. 13/156,307, filed Jun. 8, 2011.
Non-Final Office Action mailed May 27, 2014 for U.S. Appl. No. 13/156,307, filed Jun. 8, 2011.
Shrivastava A., et al., "Methods for the Determination of Limit of Detection and Limit of Quantitation of the Analytical Methods," Chronicles of Young Scientists, 2011, vol. 2 (1), pp. 21-25.

* cited by examiner

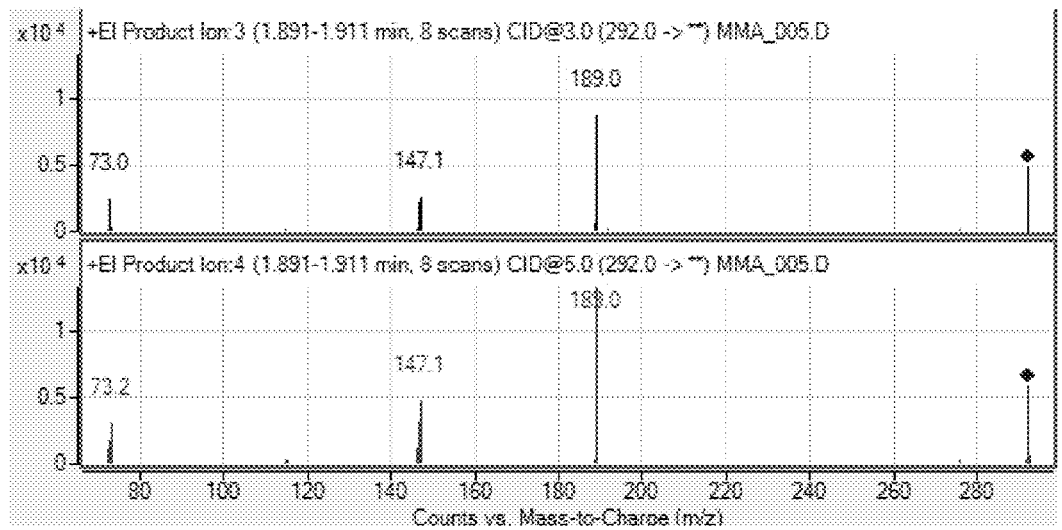
FIG 4A
FIG 4B
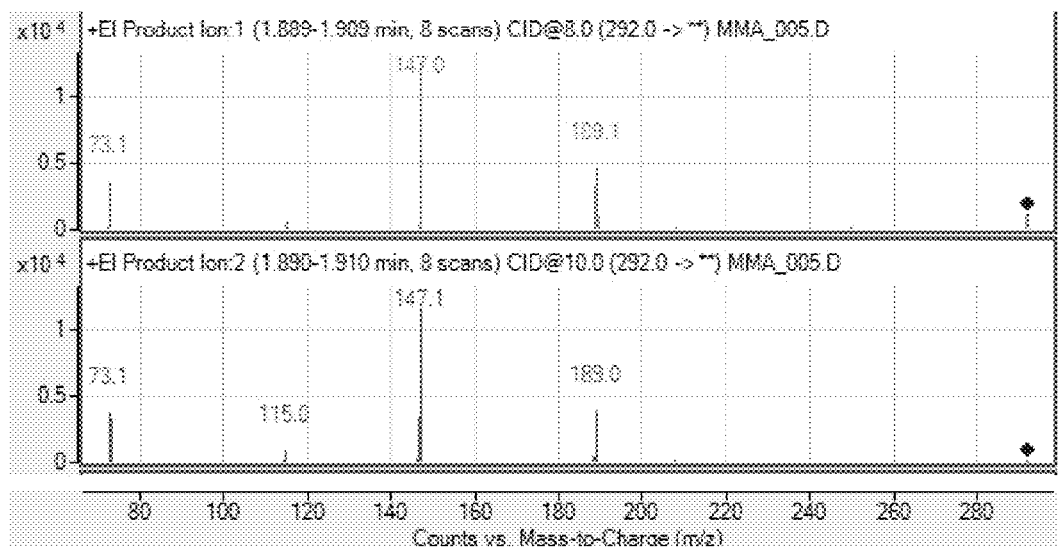
FIG 4C
FIG 4D

MASS SPECTROMETRIC DETERMINATION OF TERT-BUTYLDIMETHYLSILYL DERIVATIZED METHYLMALONIC ACID

CROSS REFERENCE TO RELATED PATENT APPLICATIONS

This application is a continuation application of U.S. application Ser. No. 13/156,307, filed Jun. 8, 2011, now U.S. Pat. No. 10,837,972, which claims the benefit of U.S. Provisional Appl. No. 61/353,172, filed Jun. 9, 2010, each of which is hereby incorporated by reference in its entirety.

FIELD OF THE INVENTION

The invention relates to the quantitative measurement of methylmalonic acid. In a particular aspect, the invention relates to methods for quantitative measurement of methylmalonic acid by gas chromatography-tandem mass spectrometry.

BACKGROUND OF THE INVENTION

Methylmalonic acid (MMA) is a C-methylated dicarboxylic acid derivative of malonate. The coenzyme A-linked form of MMA is a metabolic intermediate in the conversion of propionyl-CoA to succinyl-CoA. Vitamin $B_{12}$ is a vital co-factor in this conversion. If insufficient vitamin $B_{12}$ is available, the conversion does not proceed to completion. Build-up of incomplete conversion products (including L-methylmalonyl-CoA) ultimately leads to increased MMA production. Thus, elevated levels of MMA are observed when there is a vitamin $B_{12}$ deficiency.

Several methods for MMA determination in biological samples have been reported. For example, gas chromatography-single mass spectrometry techniques utilizing derivatization of MMA prior to analysis have been reported by Allen et al. (U.S. Pat. Nos. 5,438,017 and 5,457,055; detection of t-butyldimethylsilyl ester derivatives); Lou et al. (*J. Huazhong University of Science and Technology* (2004) 24:166-9; detection of N, o-Bis(trimethylsilyl)trifluoroacetamide derivatives); Stabler et al. (*J. Clin. Invest*. (1986) 77:1606-12; detection of t-butyldimethylsilyl ester derivatives); Marcell, et al. (*Analytical Chem*. (1985) 150:58-66; detection of t-butyldimethylsilyl ester derivatives); McCann, et al. (*Clin. Chem*. (1996) 42:910-14; detection of t-butyldimethylsilyl ester derivatives); Windelberg, et al. (*Clin. Chem*. (2005) 51:2103-09; detection of methylchloroformate derivatives); Specker, et al. (*Am J Clin Nutr*. (1990) 51:209-11; detection of dicyclohexyl ester derivatives); Yazdanpanah, et al. (*Clin Biochem*. (2003) 36:617-20; detection of N, o-Bis(trimethylsilyl)trifluoroacetamide derivatives); Purevsuren, et al. (*Brain and Develop*. (2008) 30:520-26; detection of bis(trimethylsilyl)triflurooacetamide and trimethylchlorosilane derivatives); Chen et al. (Clinical Applications of Mass Spectrometry, Methods in Molecular Biology, Chapter 35:365; detection of trimethylchlorosilane and butyl ester derivatives); and Young, et al. (*Analyst* (1995) 120:2199-2201; reporting butyl ester derivatives). Liquid chromatography-tandem mass spectrometry techniques utilizing derivatization of MMA prior to analysis have been reported by Shushan et al. (U.S. Pat. No. 6,692,971; detection of n-butyl ester derivatives); Kushnir et al. (U.S. Publication No. 2004/0165560; detection of n-butyl ester derivatives); and Kushnir et al. (*Clin. Chem*. (2001) 47:1993-2000; detection of dibutyl ether derivatives). Gas chromatography-tandem mass spectrometric techniques have been reported by Hagen, et al. (*Clinica Chimica Atca* (1999) 283:77-88; detection of trimethylsilyl derivatives); and Ueland et al. (*Clin Chem Lab Med* (2007) 445:1737-45; detection of methylchloroformate derivatives).

SUMMARY OF THE INVENTION

One aspect of the present invention provides methods for determining the amount of methylmalonic acid (MMA) in a sample by tandem mass spectrometry. In some embodiments, the methods include: (a) obtaining a sample containing MMA; (b) subjecting the MMA containing sample to a derivatizing agent under conditions suitable to generate tert-butyldimethylsilyl derivatized MMA (TBDMS-MMA); (c) subjecting TBDMS-MMA from the sample to chromatography; (d) ionizing TBDMS-MMA following chromatography to generate two or more ions detectable by mass spectrometry, these ions including a precursor ion with a mass to charge ratio of 289.0±0.5 and one or more fragment ions selected from the group consisting of fragment ions with mass to charge ratios of 189.0±0.5, 147.0±0.5, and 73.0±0.5; and (e) determining the amount of one or more fragment ions by tandem mass spectrometry. In these methods, the amount of ions determined in step (e) is related to the amount of MMA originally present in the sample. In some embodiments, chromatography is gas chromatography (GC). In some embodiments, the derivatizing agent comprises methyl-(t-butyldimethylsilyl)trifluoroacetamide (MTBSFTA). In some embodiments, MMA originally present in the sample is purified by solid phase extraction prior to being subjected to the derivatizing agent. In some embodiments, the sample is from a human patient.

In some embodiments, the methods include: (a) obtaining a sample containing MMA; (b) subjecting said sample to a derivatizing agent under conditions suitable to generate tert-butyldimethylsilyl derivatized MMA (TBDMS-MMA); (c) subjecting TBDMS-MMA from the sample to gas chromatography (GC); (d) ionizing TBDMS-MMA following chromatography to generate two or more ions detectable by mass spectrometry, the ions including a precursor ion and one or more fragment ions; and (e) determining the amount of one or more of the fragment ions by tandem mass spectrometry. In these embodiments, the amount of ions determined in step (e) is related to the amount of MMA originally present in the sample. In some embodiments, the precursor ion has a mass to charge ratio of 289.0±0.5. In some embodiments, one or more fragment ions are selected from the group consisting of fragment ions with mass to charge ratios of 189.0±0.5, 147.0±0.5, and 73.0±0.5. In some embodiments, the derivatizing agent comprises methyl-(t-butyldimethylsilyl)trifluoroacetamide (MTBSFTA). In some related embodiments, MMA in the sample is purified by solid phase extraction prior to being subjected to the derivatizing agent.

In some embodiments, the methods include: (a) obtaining a sample containing tert-butyldimethylsilyl derivatized MMA (TBDMS-MMA), wherein TBDMS-MMA is produced by derivatizing MMA originally present in the sample; (b) subjecting TBDMS-MMA from the sample to chromatography; (c) ionizing TBDMS-MMA following chromatography to generate two or more ions detectable by mass spectrometry, the ions including a precursor ion with a mass to charge ratio of 289.0±0.5 and one or more fragment ions selected from the group consisting of fragment ions with mass to charge ratios of 189.0±0.5, 147.0±0.5, and 73.0±0.5; and (d) determining the amount of one or more of the fragment ions by tandem mass spectrometry. In these embodiments, the amount of ions determined in step (d) is related to the amount of MMA originally present in the sample. In some embodiments, chromatography is gas chromatography. In some embodiments, the methods further include obtaining a sample containing MMA and subjecting the MMA containing sample to a derivatizing agent under conditions suitable to generate tert-butyldimethylsilyl derivatized MMA (TBDMS-MMA). In some related embodiments, the derivatizing agent comprises methyl-(t-butyldimethylsilyl)trifluoroacetamide (MTBSFTA). In some related embodiments, the sample is purified by solid phase extraction prior to being subjected to said derivatizing agent.

In a second aspect, methods are presented for determining the amount of tert-butyldimethylsilyl derivatized MMA (TBDMS-MMA) in a sample by tandem mass spectrometry. These methods include: (a) subjecting TBDMS-MMA in the sample to chromatography; (b) ionizing TBDMS-MMA following chromatography to generate two or more ions detectable by mass spectrometry, these ions including a precursor ion with a mass to charge ratio of 289.0±0.5 and one or more fragment ions selected from the group consisting of fragment ions with mass to charge ratios of 189.0±0.5, 147.0±0.5, and 73.0±0.5; and (c) determining the amount of one or more of the fragment ions by tandem mass spectrometry. In these methods, the amount of ions determined in step (c) is related to the amount of MMA originally present in the sample. In some embodiments, chromatography is gas chromatography.

In a third aspect, methods are presented for diagnosing vitamin $B_{12}$ deficiency in a patient. These methods include: (a) obtaining a sample containing MMA from a patient; (b) subjecting MMA from the sample to a derivatizing agent under conditions suitable to generate tert-butyldimethylsilyl derivatized MMA (TBDMS-MMA); (c) subjecting the TBDMS-MMA from step (b) to chromatography; (d) ionizing TBDMS-MMA following chromatography to generate two or more ions detectable by mass spectrometry, these ions including a precursor ion with a mass to charge ratio of 289.0±0.5 and one or more fragment ions selected from the group consisting of fragment ions with mass to charge ratios of 189.0±0.5, 147.0±0.5, and 73.0±0.5; (e) determining the amount of one or more of the fragment ions by tandem mass spectrometry; (f) determining the amount of MMA originally in the sample from the amount of ions determined in step (e); and (g) diagnosing a vitamin $B_{12}$ deficiency in the patient from the amount of MMA determined in step (f). In some embodiments, chromatography is gas chromatography. In some embodiments, the derivatizing agent comprises methyl-(t-butyldimethylsilyl)trifluoroacetamide (MTBSFTA). In some embodiments, MMA in the sample is purified by solid phase extraction prior to being subjected to said derivatizing agent.

In some embodiments, TBDMS-MMA is ionized by electron impact ionization.

In some embodiments, the sample is a biological sample, preferably a body fluid sample; for example, plasma or serum, such as from a human patient.

In the methods described herein, mass spectrometry is tandem mass spectrometry. Tandem mass spectrometry may be conducted by any method known in the art, including for example, multiple reaction monitoring, precursor ion scanning, or product ion scanning.

As used herein, "derivatizing" means reacting two molecules to form a new molecule. Thus, a derivatizing agent is an agent that may be reacted with another substance to derivatize the substance. For example, methyl-(t-butyldimethylsilyl)trifluoroacetamide (MTBSFTA) is a derivatizing reagent that may be reacted with MMA to form tert-butyldimethylsilyl derivatized MMA (TBDMS-MMA).

As used here, the names of derivatized forms of MMA include an indication as to the nature of derivatization. For example, tert-butyldimethylsilyl derivatized MMA is indicated as TBDMS-MMA (or TBDMS-derivatized MMA).

In certain embodiments, mass spectrometry is performed in positive ion mode. Alternatively, mass spectrometry is performed in negative ion mode. Various ionization sources, including for example electron impact (EI) ionization, atmospheric pressure chemical ionization (APCI), laser diode thermal desorption (LDTD), or electrospray ionization (ESI), may be used in embodiments of the present invention. In some embodiments, TBDMS-MMA is ionized by EI in positive ion mode.

One or more separately detectable internal standards may be provided in the sample prior to treatment of the sample with a derivatizing reagent. In these embodiments, the one or more internal standards may undergo derivatization along with the endogenous MMA, in which case ions of the derivatized internal standards are detected by mass spectrometry. Alternatively, the one or more separately detectable internal standards may be provided in the sample after treatment with a derivatizing reagent. The presence or amount of ions generated from the analyte of interest may be related to the presence or amount of analyte of interest in the sample by comparison to the amount of ions generated from the internal standard(s). In some embodiments, the internal standards may be isotopically labeled versions of MMA, such as MMA-$^2$H$_3$.

Ions detectable in a mass spectrometer may be generated for any internal standard selected for use. Exemplary spectra generated for TBDMS-MMA-$^2$H$_3$ are discussed in Example 3, and shown in FIGS. 4A-G.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. For example, MMA-$^2$H$_3$ has a mass of about 3 mass units higher than MMA. The isotopic label can be incorporated at one or more positions in the molecule and one or more kinds of isotopic labels can be used on the same isotopically labeled molecule.

In other embodiments, the amount of TBDMS-MMA ion or ions may be determined by comparison to one or more external reference standards. Exemplary external reference standards include blank plasma or serum spiked with TBDMS-MMA or an isotopically labeled version thereof. External standards typically will undergo the same treatment and analysis as any other sample to be analyzed.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

As used herein, the term "chromatography" refers to a process in which a chemical mixture carried by a liquid or gas is separated into components as a result of differential distribution of the chemical entities as they flow around or through a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (such as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm.

As used herein, the term "analytical column" refers to a chromatography column having sufficient chromatographic plates to effect a separation of materials in a sample that elute from the column sufficient to allow a determination of the presence or amount of an analyte. In a preferred embodiment the analytical column contains particles of about 5 μm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer* and *Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron impact" ionization or "EI" ionization refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 3A shows product ion spectra for CID at 3. FIG. 3B shows product ion spectra for CID at 5. FIG. 3C shows product ion spectra for CID at 8. FIG. 3D shows product ion spectra for CID at 10. FIG. 3E shows product ion spectra for CID at 12. FIG. 3F shows product ion spectra for CID at 15. FIG. 3G shows product ion spectra for CID at 18. Details are described in Example 3.

FIGS. 4A-4G show exemplary product ion spectra (covering the m/z range of about 60 to 300) for fragmentation of the TBDMS-MMA-$^2H_3$ precursor ion with m/z of about 292.0 at various collision energies. FIG. 4A shows product ion spectra for CID at 3. FIG. 4B shows product ion spectra for CID at 5. FIG. 4C shows product ion spectra for CID at 8. FIG. 4D shows product ion spectra for CID at 10. FIG. 4E shows product ion spectra for CID at 12.

FIG. 4F shows product ion spectra for CID at 15. FIG. 4G shows product ion spectra for CID at 18. Details are described in Example 3.

FIG. 9A shows a plot of values obtained from the same sample by each method, while FIG. 9B shows the differences between obtained values as a function of MMA concentration. Details are discussed in Example 8.

DETAILED DESCRIPTION OF THE INVENTION

Figure 1A:
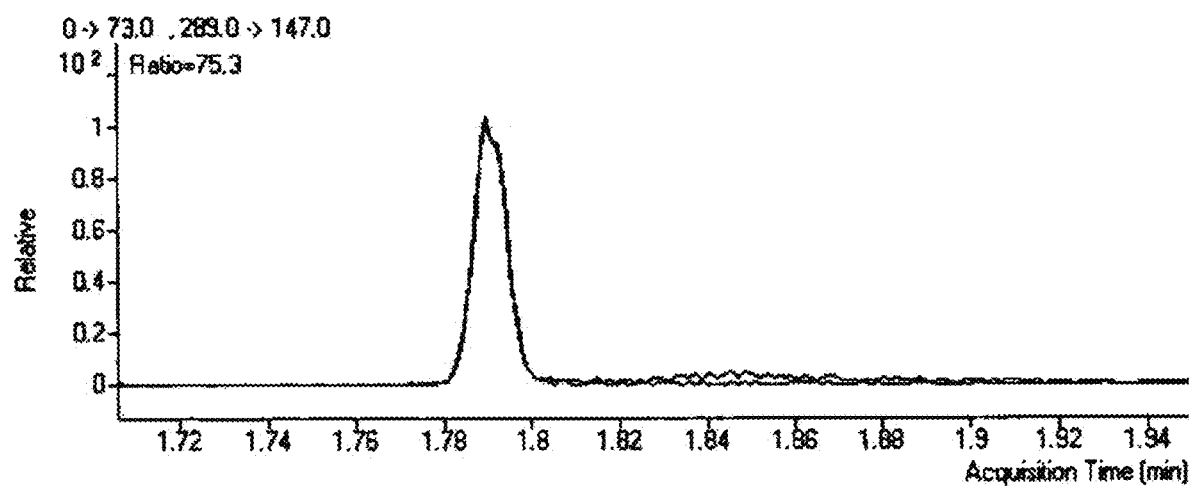
FIG. 1A shows exemplary chromatogram for TBDMS-MMA.

Methods are described for determining the amount of MMA in a sample. More specifically, tandem mass spectrometric methods are described for detecting and quantifying tert-butyldimethylsilyl derivatized MMA (TBDMS-MMA) in a sample. Thus, the amount of MMA in a sample may be determined by derivatizing MMA in a sample to form TBDMS-MMA, measuring the amount of TBDMS-MMA in the sample by tandem mass spectrometry, and relating the amount of TBDMS-MMA measured to the amount of MMA in the sample. In some embodiments, TBDMS-MMA derivatives may be prepared by derivatization of MMA with methyl-(t-butyldimethylsilyl)trifluoroacetamide (MTBSFTA).

The methods may use a chromatography technique, such as gas chromatography (GC), to perform a purification of derivatized MMA, combined with methods of mass spectrometry (MS), thereby providing a high-throughput assay system for detecting and quantifying MMA in a sample. Preferred embodiments are particularly well suited for application in large clinical laboratories for automated MMA quantitation.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma (including EDTA and heparin plasma) and serum; most preferably serum. Such samples may be obtained, for example, from a patient; that is, a living person, male or female, presenting oneself in a clinical setting for diagnosis, prognosis, or treatment of a disease or condition.

The present invention also contemplates kits for a MMA quantitation assay. A kit for a MMA quantitation assay may include a kit comprising the compositions provided herein. For example, a kit may include packaging material and measured amounts of derivatizing reagent for generation of TBDMS-MMA derivatives (such as MTBSFTA) and an isotopically labeled internal standard, in amounts sufficient for at least one assay. Typically, the kits will also include instructions recorded in a tangible form (e.g., contained on paper or an electronic medium) for using the packaged reagents for use in a MMA quantitation assay.

Calibration and QC pools for use in embodiments of the present invention are preferably prepared using a matrix similar to the intended sample matrix.

As described above, elevated MMA levels may be caused in a patient by a vitamin $B_{12}$ deficiency. Therefore, some embodiments of the present invention may be used to diagnose vitamin $B_{12}$ deficiency in a patient, or monitor compliance with and/or efficacy of treatment of vitamin $B_{12}$ deficiency in a patient. For example, detection of MMA levels in excess of about [[223±20 nMol/L (Please Confirm)]] are indicative of vitamin $B_{12}$ deficiency.

Sample Preparation for Mass Spectrometric Analysis

In preparation for mass spectrometric analysis, MMA may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving MMA in the supernatant. The samples may be centrifuged to separate the liquid supernatant from the precipitated proteins; alternatively the samples may be filtered to remove precipitated proteins. The purified MMA may then be derivatized with reagent capable of generating TBDMS-MMA, preferably MTBSFTA or an isotopically labeled variant thereof.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with derivatized vitamin D. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with derivatized MMA. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained (i.e., solid phase extraction). In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

Another method of sample purification that may be used prior to mass spectrometry is gas chromatography (GC) (also sometimes known as vapor-phase chromatography or liquid partition chromatography). Gas chromatography may be employed in methods of analyzing compounds that can be vaporized without decomposition. In gas chromatography, the mobile phase is a carrier gas, usually an inert gas such as helium or an unreactive gas such as nitrogen. The stationary phase is a microscopic layer of liquid or polymer on an inert solid support. The stationary phase is contained inside a column. The gaseous compounds being analyzed interact with the walls of the column, which may be coated with various stationary phases. Varying degrees of interaction of each gaseous compound with the stationary phase cause each compound to elute at a different times. Thus, for a given stationary phase and given column conditions, each compound will have a characteristic retention time. In some embodiments, a GC column comprising cyanopropyl methyl siloxane, such as an Agilent DB-23 cis/trans FAME GC column, is used to purify TBDMS-MMA. In some embodiments, the carrier gas is helium. In some embodiments, the column is heated to a temperature of about 185° C. and held for about 0.4 minutes, then the temperature is ramped to about 300° C.; for example at a rate of about 85° C./minute. Once the temperature reaches about 300° C., the temperature is then held constant, for example for about 0.6 minutes.

In some embodiments, an extraction column may be used for purification of MMA prior to mass spectrometry. In such embodiments, MMA is purified by applying a first mobile phase (containing the analyte) to an extraction column which captures the analyte, and then eluting the captured analyte with a second mobile phase. The eluent may be collected and chromatographed on a second extraction column or on an analytical column (such as a GC column) prior to ionization. In some embodiments, extraction of MMA via extraction column is done before MMA is derivatized; alternatively, MMA may be derivatized prior to extraction.

Detection and Quantitation by Mass Spectrometry

In various embodiments, derivatized MMA may be ionized by any method known to the skilled artisan. Mass spectrometry is performed using a mass spectrometer, which includes an ion source for ionizing the fractionated sample and creating charged molecules for further analysis. For example ionization of the sample may be performed by electron impact (EI) ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Derivatized MMA may be ionized in positive or negative mode. In preferred embodiments, derivatized MMA is ionized by electron impact (EI) ionization in positive mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain embodiments, an internal standard is used to generate a standard curve for calculating the quantity of MMA. Methods of generating and using such standard curves are well known in the art and one of ordinary skill is capable of selecting an appropriate internal standard. For example, in some embodiments an isotopically labeled MMA (e.g., MMA-$^2$H$_3$) may be used as an internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, MMA in a sample is detected and/or quantified using MS/MS as follows. MMA is first extracted from a sample with a solid phase extraction column. Then, MMA in the purified sample is derivatized with a reagent capable of generating TBDMS-MMA, preferably MTBSFTA. The purified samples (now comprising TBDMS-MMA) are then subjected to gas chromatography; the flow of analyte from the chromatographic column enters an EI ionization source and TBDMS-MMA ions are generated. The TBDMS-MMA ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their bases to charge ratio (m/z). Quadrupole 2 (Q2) is the collision cell, where ions are fragmented. The first quadrupole of the mass spectrometer (Q1) selects for TBDMS-MMA precursor ions, which are allowed to pass into the collision chamber (Q2), while unwanted ions with any other mass/charge ratio collide with the sides of the quadrupole and are eliminated. Precursor ions entering Q2 collide with a collision gas and fragment. The fragment ions generated are passed into quadrupole 3 (Q3), where certain TBDMS-MMA fragment ions are selected while other ions are eliminated.

As ions collide with the detector they produce a pulse of electrons that are converted to a digital signal. The acquired data is relayed to a computer, which plots counts of the ions collected versus time. The resulting mass chromatograms are similar to chromatograms generated in traditional GC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of MMA. As described above, the relative abundance of a given ion may be converted into an absolute amount of the original analyte using calibration standard curves based on peaks of one or more ions of an internal molecular standard.

EXAMPLES

Example 1: Solid Phase Extraction and TBDMS Derivatization

The following extraction techniques were conducted on serum samples.

MMA was extracted from serum samples by solid phase extraction (SPE) on a strong anion exchange (SAX) packed SPE column. Water and 100% methanol were used as wash and elution solvents, respectively. Alternatively, MMA was extracted from serum samples by SPE on a SAX packed SPE column where water and 3 M acetic acid/methanol were used as wash and elution solvents, respectively.

MMA was then derivatized by adding 150 µl of MTBSTFA with 1% tert-butyl dimethylchlorosilane (TBDMCS) in hexane or pyridine to the collected extracted samples. The resulting mixtures were heated to about 70° C. for 15-20 minutes and chilled at about 4° C. for about 10 minutes. After cooling, the mixtures were transferred to GC/MS vials for analysis.

Alternatively, MMA from the sample was derivatized by first evaporating the eluted samples to dryness, adding 500 µl of 20% triethylamine in methanol to the dried samples, drying the samples again, adding 100 µl MTBSTFA with 1% tert-butyl dimethylchlorosilane (TBDMCS) in hexane or pyridine to the dried samples, and vortexing for 2-3 minutes. The resulting mixtures were heated to about 60° C. for about 30 minutes and then chilled. After cooling, the mixtures were then subjected to GC-MS/MS analysis.

Example 2: Purification of TBDMS-MMA Derivatives with Gas Chromatography

Purification of TBDMS-MMA derivatives with gas chromatography was conducted with an Agilent 7890A Fast GC equipped with a cyanopropyl methyl siloxane analytical column, such as an Agilent DB-23 cis/trans FAME GC column (DB-23: J&W 122-2361, Agilent Technologies, Wilmington, DE USA). The GC column was heated to a temperature of about 185° C. and held for about 0.4 minutes. The GC column was then heated further to a temperature of about 300° C. at a rate of about 85° C./minute. Once the temperature reached about 300° C., the temperature was held at about 300° C. for about 0.6 minutes. Helium was used as the carrier gas at approximately 3 ml/min. Under these conditions, retention time for TBDMS-MMA was about 1.76-1.78 minutes. Succinic acid, a potentially interfering species with a similar mass to MMA, was clearly separated from MMA under this procedure with a retention time of approximately 2.12 minutes.

Alternatively, purification of TBDMS-MMA derivatives with gas chromatography was conducted with an Agilent 7890 GC equipped with a cyanopropyl methyl siloxane analytical column, such as an Agilent DB-23 cis/trans FAME GC column (DB-23: J&W 122-2361, Agilent Technologies, Wilmington, DE USA). The GC column was heated to a temperature of about 300° C. Helium was used as the carrier gas at approximately 4 ml/min. Under these conditions, retention time for TBDMS-MMA was about 1.30 minutes.

Example 3: Detection and Quantitation of TBDMS-MMA Derivatives by MS/MS

MS/MS was performed on the above generated samples using a Agilent 7001 GC/MS Triple Quadrupole MS system (Agilent Technologies, Wilmington, DE USA). TBDMS-MMA exiting the analytical column flowed to the electron impaction ionization interface of the MS/MS analyzer and ionized.

Ions passed to the first quadrupole (Q1), which selected TBDMS-MMA precursor ions with a mass-to-charge ratio of 289.0±0.5 m/z. Ions entering quadrupole 2 (Q2) collided with argon gas to generate ion fragments, which were passed to quadrupole 3 (Q3) for further selection. Simultaneously, the same process using isotope dilution mass spectrometry was carried out with internal standard, TBDMS-MMA-$^2H_3$. Mass transitions observed at collision energies of 3V and 10 V (positive polarity) are shown in Table 1.

TABLE 2

Mass Transitions for TBDMS-MMA and TBDMS-MMA-$^2H_3$ (internal standard) (Positive Polarity)

| Analyte | Precursor Ion (m/z) | Product Ions (m/z) (CE = 3 V) | Product Ions (m/z) (CE = 10 V) |
|---|---|---|---|
| TBDMS-MMA | 289.0 ± 0.5 | 189.0 ± 0.5 | 147.0 ± 0.5 |
|  |  | 147.0 ± 0.5 | 73.0 ± 0.5 |
|  |  | 73.0 ± 0.5 |  |
| TBDMS-MMA-$^2H_3$ | 292.0 ± 0.5 | 189.0 ± 0.5 | 147.0 ± 0.5 |
|  |  | 147.0 ± 0.5 | 73.0 ± 0.5 |
|  |  | 73.0 ± 0.5 |  |

Figure 1B:
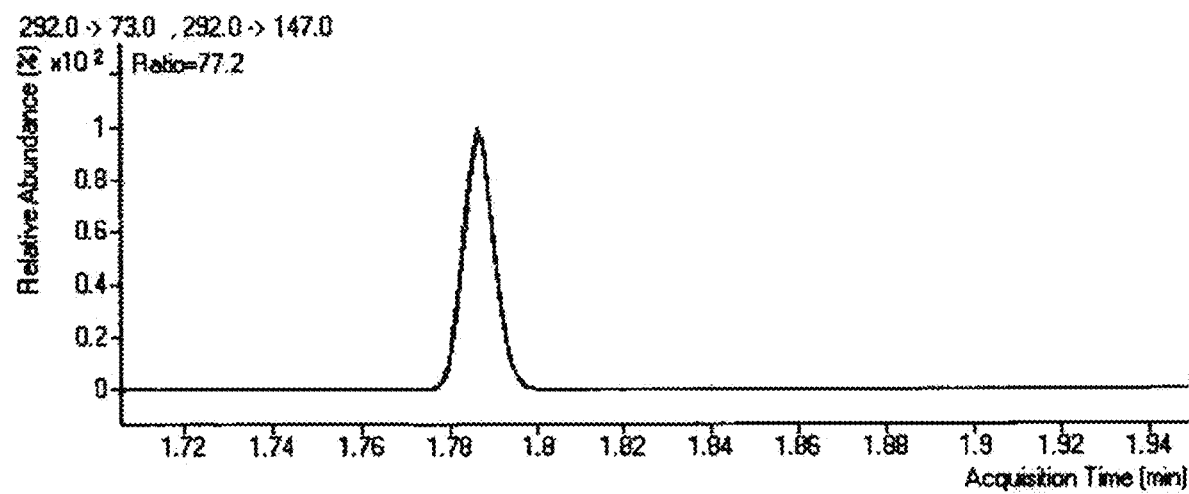
FIG. 1B shows exemplary chromatogram for TBDMS-MMA-$^2H_3$ (internal standard). Details are discussed in Example 3.

Exemplary chromatograms for TBDMS-MMA and TBDMS-MMA-$^2H_3$ (internal standard), are shown in FIGS. 1A and 1B, respectively.

Figure 2:
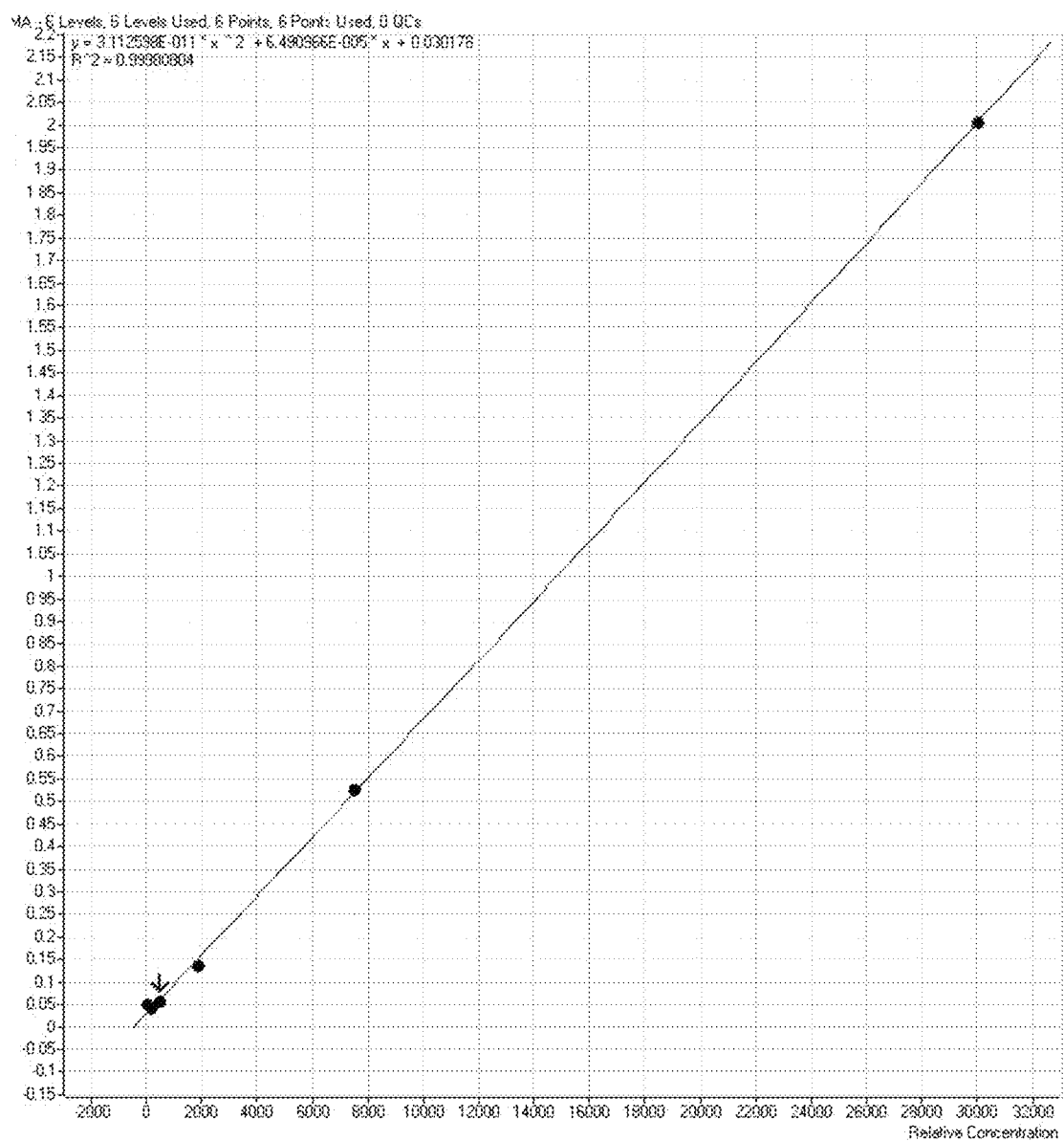
FIG. 2 shows an exemplary calibration curve for MMA determined by methods described in Example 3.
Figure 3A:
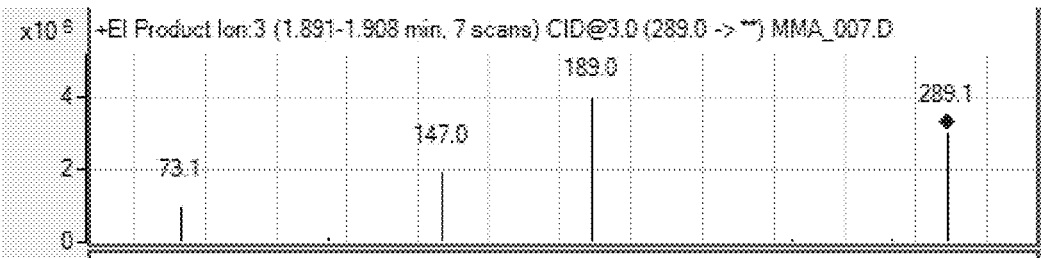
FIGS. 3A-3G show exemplary product ion spectra (covering the m/z range of about 50 to 310) for fragmentation of the TBDMS-MMA precursor ion with m/z of about 289.0 at various collision energies.
Figure 3B:
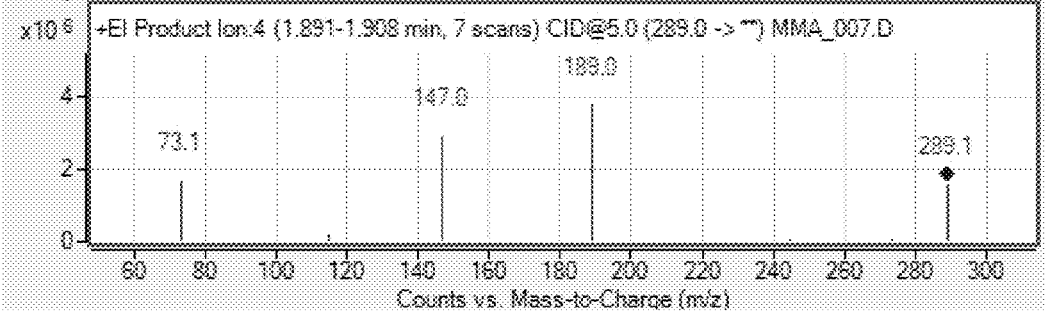
Figure 3C:
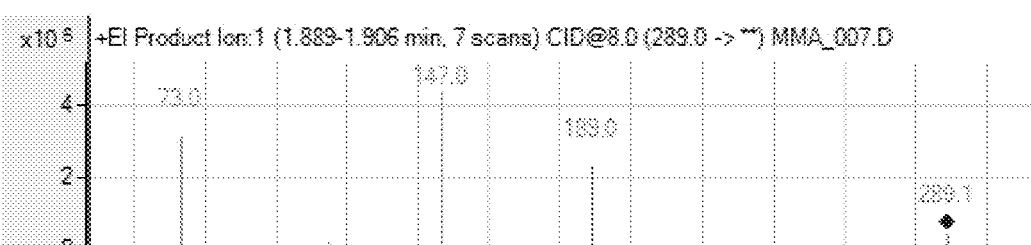
Figure 3D:
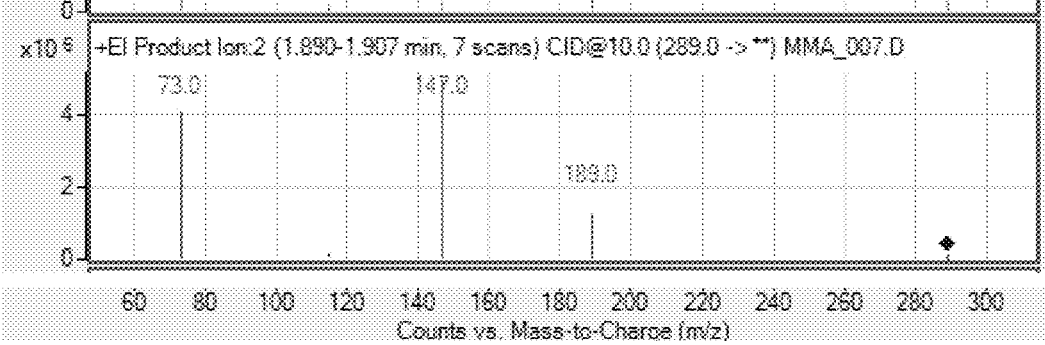
Figure 3E:
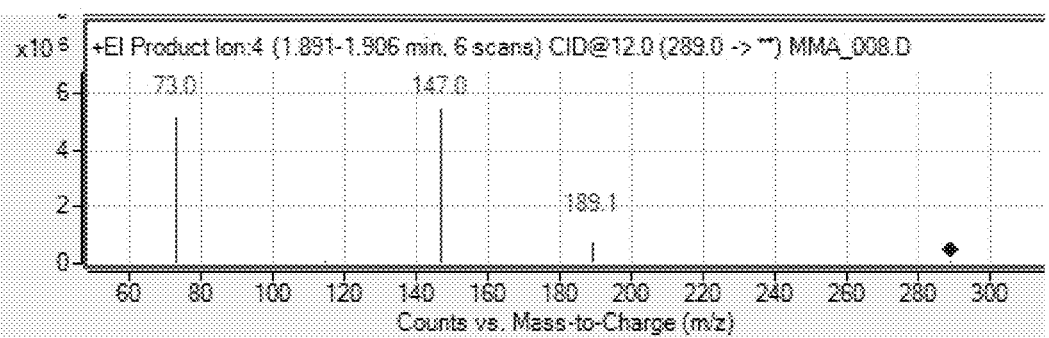
Figure 3F:
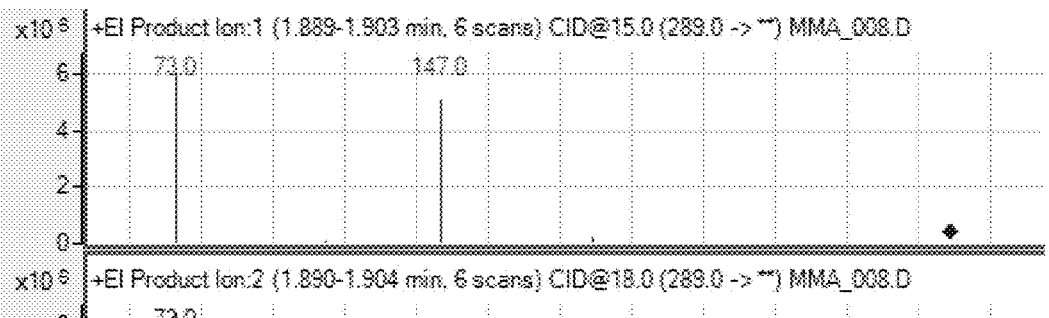
Figure 3G:
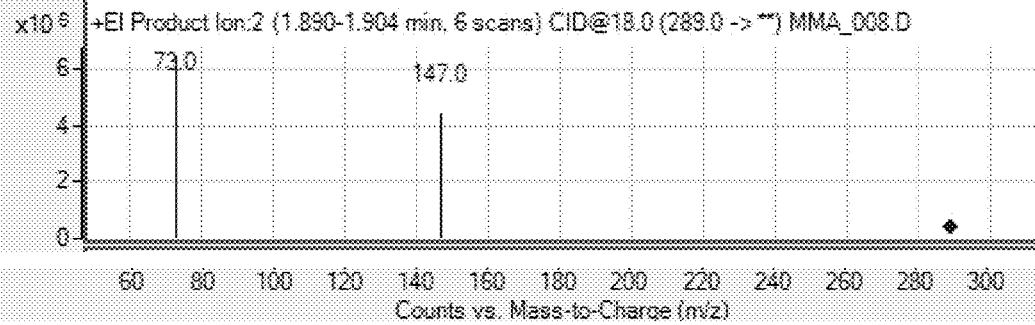
Figure 4E:
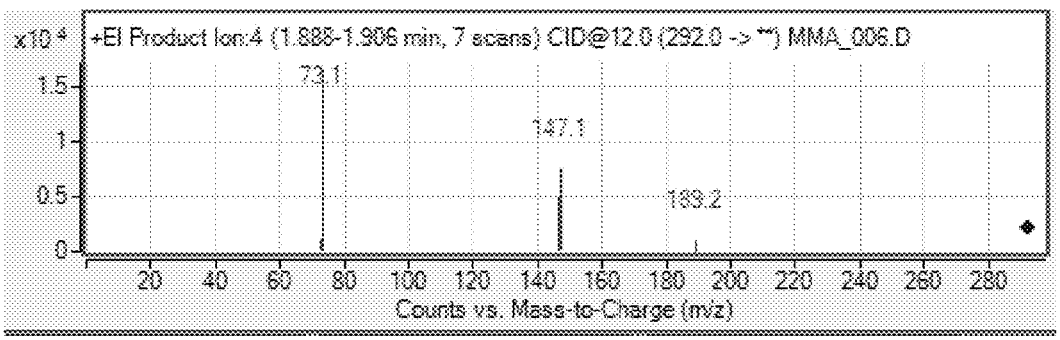
Figure 4F:
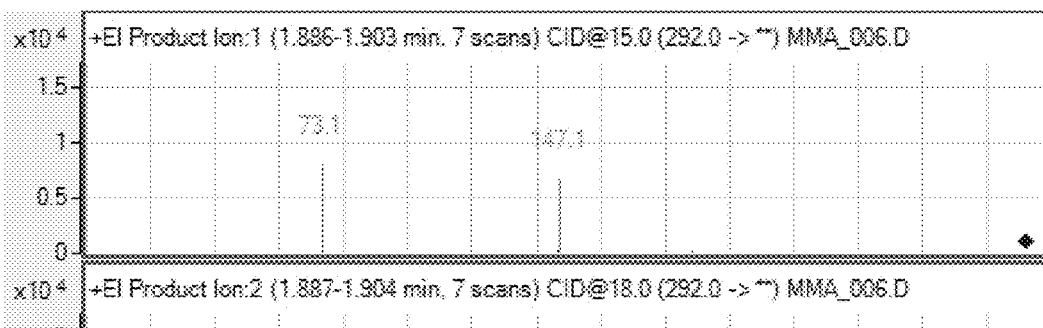
Figure 4G:
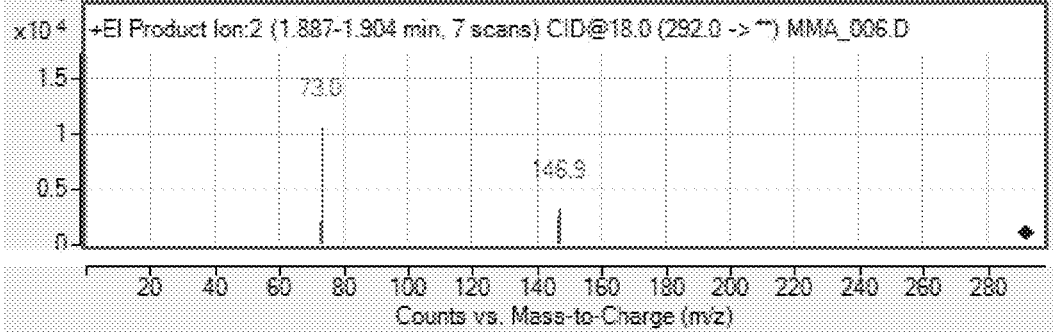

An exemplary calibration curve for the determination of TBDMS-MMA in serum as measured by monitoring the transition from 289.0±0.5→147.0±0.5 at a collision energy of about 10 V is shown in FIG. 2.

Example 3: Exemplary Spectra from MS/MS Analysis of TBDMS-MMA

Tandem mass spectrometric analyses of TBDMS-MMA and TBDMS-MMA-$^2$H$_3$ were conducted by selecting precursor ions with m/z of about 289.0 and 292.0, respectively. The precursor ions were fragmented at collision energies of 3, 5, 8, 10, 12, 15, and 18 V. Exemplary product ion scans generated from these analyses are presented in FIGS. 3A-3G and 4A-4G for TBDMS-MMA and TBDMS-MMA-$^2$H$_3$, respectively.

Exemplary MRM transitions for the quantitation of TBDMS-MMA include fragmenting a precursor ion with a m/z of about 289.0±0.5 to one or more product ions selected from the group of ions with a m/z of about 189.0±0.5, 147.0±0.5, and 73.0±0.5. As seen in FIGS. 3A-3G and 4A-4G, selection of fragments to monitor for quantitation may depend on the collision energy selected. At a higher collision energy, such as 10 V, fragment ions may include ions with m/z of about 147.0±0.5 and 73.0±0.5, while at lower collision energies, such as about 3 V, fragment ions may also include ions with m/z of about 189.0±0.5. Similarly, MRM transitions for the quantitation of TBDMS-MMA-$^2$H$_3$ include fragmenting a precursor ion with a m/z of about 292.0 to one or more product ions selected from the group of ions with a m/z of about 189.0±0.5, 147.0±0.5, and 73.0±0.5. Again, at a higher collision energy, such as 10 V, fragment ions may include ions with m/z of about 147.0±0.5 and 73.0±0.5, while at lower collision energies, such as about 3 V, fragment ions may also include ions with m/z of about 189.0±0.5.

Figure 5:
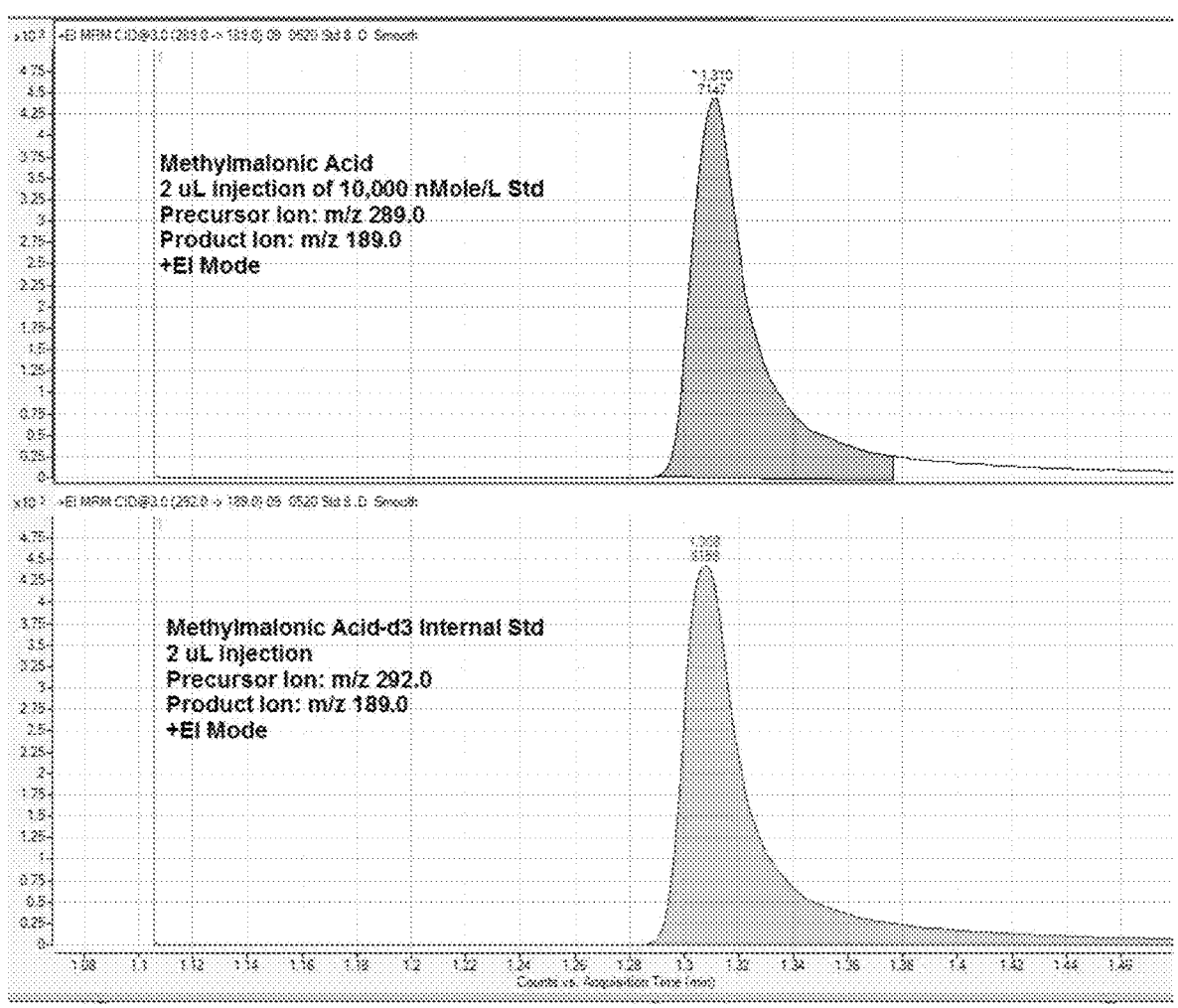
FIG. 5 shows exemplary data collected for TBDMS-MMA and TBDMS-MMA-$^2H_3$ for the m/z transitions at 289→189 (at 3 V) and 292→189 (at 3 V), respectively. Details are discussed in Example 3.
Figure 6:
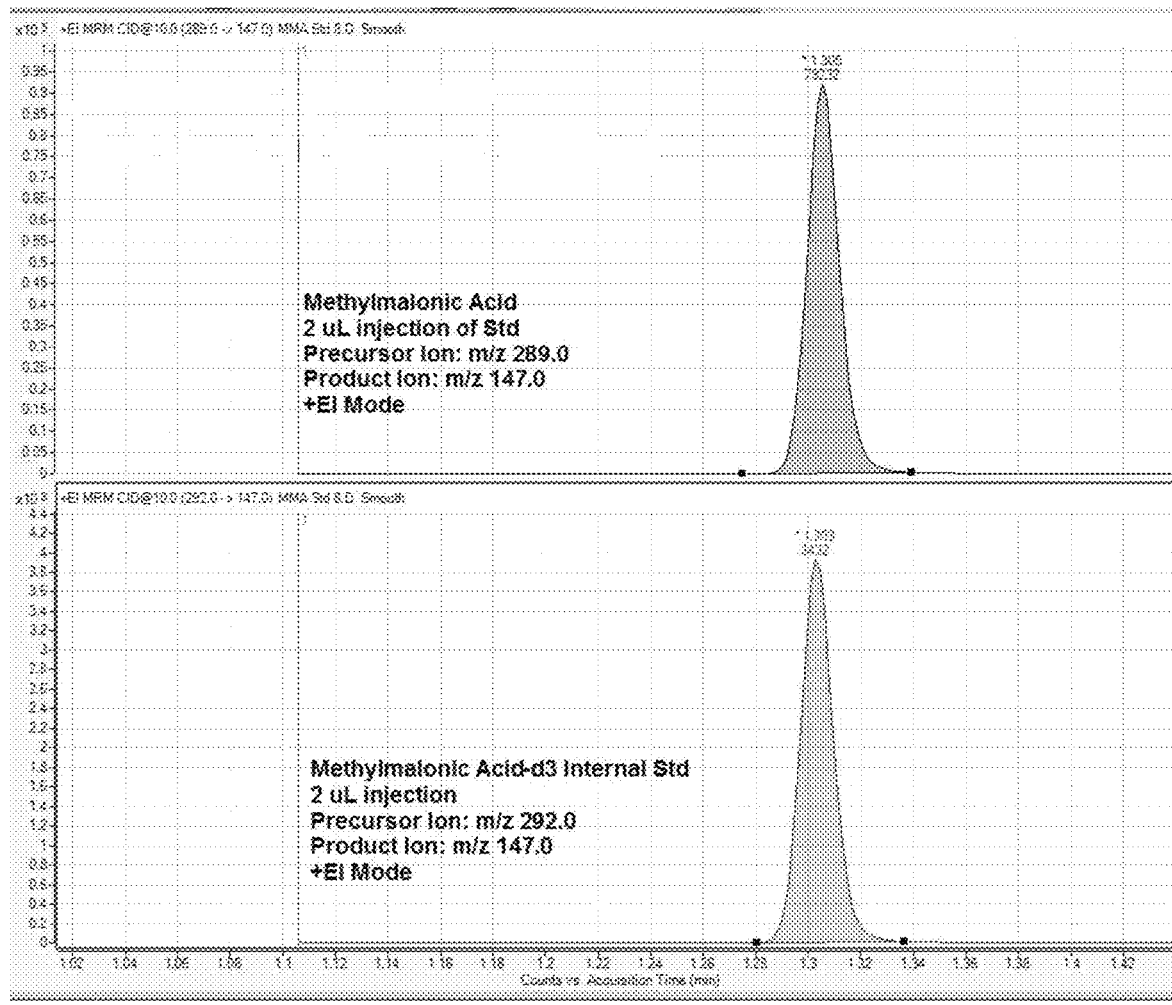
FIG. 6 shows exemplary data collected for TBDMS-MMA and TBDMS-MMA-$^2H_3$ for the m/z transitions at 289→147 (at 10 V) and 292→147 (at 10 V), respectively. Details are discussed in Example 3.

Data was collected for quantitation of TBDMS-MMA and TBDMS-MMA-$^2$H$_3$ in serum by monitoring MRM transitions generated by collision energies of 3 V and 10 V. Exemplary data from the 3 V collision energy (TBDMS-MMA: 289.0→189.0; and TBDMS-MMA-$^2$H$_3$: 292.0→189.0) are shown in FIG. 5, while exemplary data from the 10 V collision energy (TBDMS-MMA: 289.0→147.0; and TBDMS-MMA-$^2$H$_3$: 292.0→147.0) are shown in FIG. 6.

Example 4: Within Run and Total Precision Studies

For within run and total precision studies, Low, Mid, and High concentration control pools were prepared with target values of 150, 1000, and 5000 nMol/L MMA by spiking charcoal stripped serum with MMA in water. MMA was quantitated in these serum samples as described above, by monitoring the MRM transition from a MRM precursor ion with m/z of about 289.0±0.5 to a fragment ion with m/z of about 189.0±0.5 (collision energy about 3 V).

For the within run precision studies, aliquots of the Low, Mid, and High control pools were analyzed 10 times each in a single sample run. The coefficients of variation (CV) from each concentration were used to determine if reproducibility within run was acceptable. Statistical analysis of the results determined that the CV for the Low, Mid, and High pools were about 2.0%, 2.7%, and 2.2%, respectively. In addition, standard deviations (SD) for each of the pools were calculated to be about 3 nMol/L, 28 nMol/L, and 111 nMol/L, respectively. Data from these experiments are presented in Table 3.

TABLE 3

Within Run Precision

| | Control Pool | | |
|---|---|---|---|
| | Low (150 nMol/L) | Mid (1000 nMol/L) | High (5000 nMol/L) |
| Replicate | Measured MMA Concentration (nMol/L) | | |
| 1 | 153 | 1054 | 4960 |
| 2 | 153 | 1033 | 5181 |
| 3 | 156 | 1028 | 4984 |
| 4 | 157 | 997 | 4952 |
| 5 | 151 | 1070 | 4961 |
| 6 | 154 | 1037 | 5191 |
| 7 | 149 | 1011 | 4855 |
| 8 | 159 | 1028 | 5021 |
| 9 | 155 | 1090 | 4965 |
| 10 | 154 | 1021 | 5130 |
| Mean | 154 | 1037 | 5020 |
| Std Dev | 3 | 28 | 111 |
| CV | 2.0% | 2.7% | 2.2% |

For the total precision studies, aliquots of the Low, Mid, and High control pools were analyzed on 19 separate days. On 17 of those days, the control pools were run in duplicate, while on two of the days, the controls were run in singleton. A total of 36 data points for each control pool were generated and statistically analyzed. The CV for the Low, Mid, and High pools were calculated to be about 10.9%, 9.3%, and 8.0%, respectively. In addition, SD for each of the pools were calculated to be about 19 nMol/L, 104 nMol/L, and 420 nMol/L, respectively. Data from these experiments are presented in Table 4.

TABLE 4

Total Precision

| | Control Pool | | |
|---|---|---|---|
| | Low (150 nMol/L) | Mid (1000 nMol/L) | High (5000 nMol/L) |
| Replicate | Measured MMA Concentration (nMol/L) | | |
| A | 153 | 1054 | 4960 |
| B | 154 | 1021 | 5130 |
| A | 150 | 1026 | 4731 |
| B | 148 | 966 | 4765 |
| A | 156 | 1056 | 5294 |
| B | 147 | 977 | 5061 |
| A | 149 | 1074 | 5279 |
| B | 181 | 1173 | 5341 |
| A | 186 | 1184 | 5684 |
| B | 177 | 1020 | 5059 |
| A | 169 | 1139 | 5158 |
| B | 181 | 1141 | 4634 |
| A | 180 | 1182 | 5164 |
| B | 157 | 1021 | 4616 |
| A | 178 | 1179 | 5382 |
| B | 156 | 1021 | 4743 |
| A | 164 | 1132 | 5280 |
| B | 151 | 1125 | 5423 |
| A | 184 | 1209 | 5805 |
| B | 185 | 1155 | 5224 |
| A | 191 | 1097 | 5461 |
| B | 180 | 1182 | 4924 |
| A | 168 | 987 | 5127 |
| B | 193 | 1197 | 4912 |
| A | 171 | 964 | 4672 |
| A | 163 | 1093 | 5044 |
| B | 174 | 1464 | 5903 |
| A | 200 | 1200 | 5269 |
| B | 175 | — | — |
| A | 180 | 1088 | 5603 |
| B | 147 | 1170 | 5660 |
| A | 175 | 1125 | 4600 |

TABLE 4-continued

Total Precision

| | Control Pool | | |
|---|---|---|---|
| | Low (150 nMol/L) | Mid (1000 nMol/L) | High (5000 nMol/L) |
| Replicate | Measured MMA Concentration (nMol/L) | | |
| B | 141 | 1143 | 5573 |
| A | 223 | 1261 | 6400 |
| B | 197 | 1273 | 5526 |
| A | 203 | 1252 | 5876 |
| B | 163 | 1236 | 5677 |
| Count (n) | 37 | 36 | 36 |
| Mean | 172 | 1127 | 5249 |
| Std Dev | 19 | 104 | 420 |
| CV | 10.9% | 9.3% | 8.0% |

Example 5: Analytical Sensitivity: Limit of Blank (LOB), Limit of Detection (LOD), and Lower Limit of Quantitation (LLOQ)

The Limit of Blank (LOB) was determined by analyzing a zero calibrator (i.e., a blank of stripped serum) 20 times in a single run. The LOB was calculated to be about 8 nMol/L.

The Limit of Detection (LOD) is the point at which a value is beyond the uncertainty associated with its measurement and is defined as four standard deviations from the zero concentration. To determine the LOD, a blank of stripped serum was analyzed 20 times in a single sample run, and the mean and SD were determined. The resulting LOD was calculated to be about 9 mMol/L.

Figure 7:
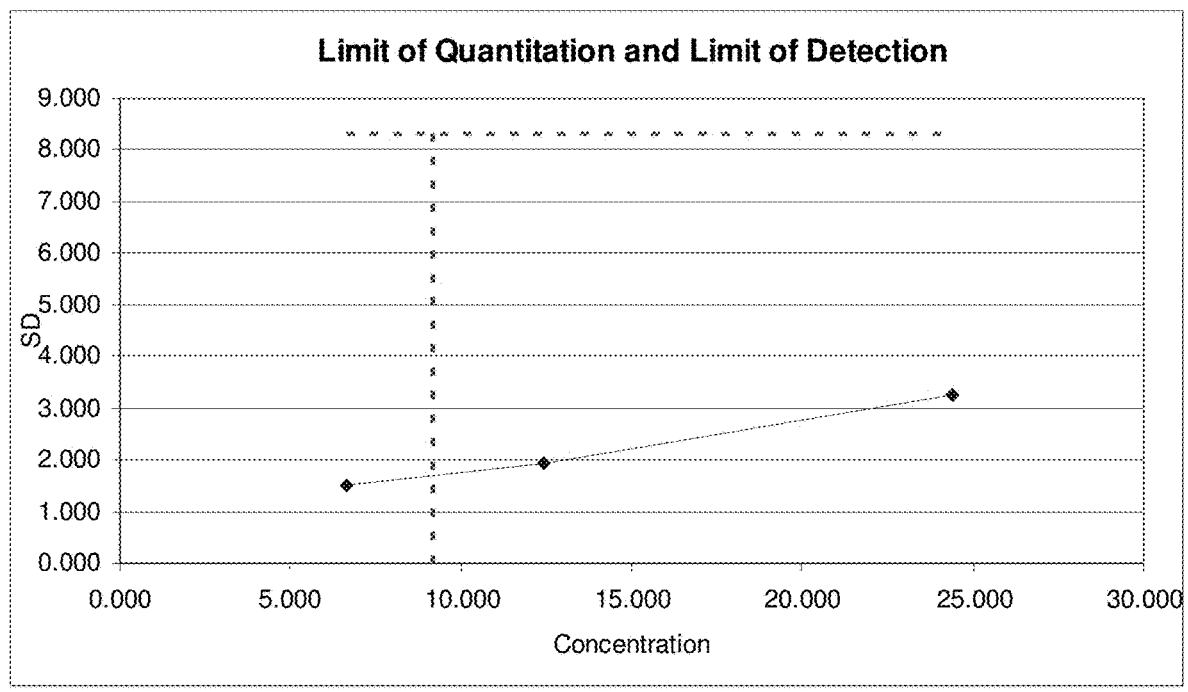
FIG. 7 shows a plot of coefficient of variation (CV) versus concentration for quantitation of TBDMS-MMA in serum measured by monitoring the m/z transition at 289→189 (at 3 V). Details are discussed in Example 5.

The Lower Limit of Quantitation (LLOQ) is the point where measurements become quantitatively meaningful. Analyte response at the LLOQ is identifiable, discrete and reproducible with a precision (i.e., coefficient of variation (CV)) of less than 20% and an accuracy of 80% to 120%. The LLOQ was determined by assaying five different stripped serum samples spiked with MMA at about 6 nMol/L, 13 nMol/L, 25 nMol/L, 50 nMol/L, and 100 nMol/L in 5 replicates over 5 days, according to the method described above in Example 4. CV's were calculated for each level. The LLOQ was calculated from the data to be 9 mMol/L. Data from analysis of the lower three concentrations and a blank are presented in Table 5. The graphical representations of CV versus concentration is shown in FIG. 7.

TABLE 5

Lower Limit of Quantitation Experiments

| | | MMA Concentration (nMol/L) | | | |
|---|---|---|---|---|---|
| Run # | Result # | 6 mMol/L | 13 mMol/L | 25 mMol/L | 0 mMol/L |
| 1 | 1 | 8.000 | 9.000 | 25.000 | 6.760 |
| | 2 | 8.000 | 10.000 | 21.000 | 8.562 |
| | 3 | 8.000 | 12.000 | 19.000 | 7.110 |
| | 4 | 8.000 | 14.000 | 25.000 | 6.492 |
| | 5 | 4.000 | 13.000 | 26.000 | 6.232 |
| 2 | 1 | 8.000 | 11.000 | 25.000 | 7.243 |
| | 2 | 7.000 | 13.000 | 20.000 | 6.208 |
| | 3 | 5.000 | 13.000 | 24.000 | 6.684 |
| | 4 | 6.000 | 13.000 | 22.000 | 6.794 |
| | 5 | 7.000 | 12.000 | 23.000 | 7.661 |
| 3 | 1 | 4.000 | 10.000 | 25.000 | 6.339 |
| | 2 | 5.000 | 10.000 | 24.000 | 6.901 |
| | 3 | 5.000 | 12.000 | 20.000 | 6.329 |
| | 4 | 4.000 | 10.000 | 19.000 | 6.967 |
| | 5 | 5.000 | 11.000 | 26.000 | 7.082 |
| 4 | 1 | 7.000 | 16.000 | 28.000 | 6.811 |
| | 2 | 6.000 | 12.000 | 29.000 | 6.994 |
| | 3 | 7.000 | 13.000 | 25.000 | 7.578 |
| | 4 | 6.000 | 12.000 | 20.000 | 7.127 |
| | 5 | 7.000 | 12.000 | 26.000 | 7.003 |
| 5 | 1 | 8.000 | 15.000 | 31.000 | — |
| | 2 | 8.000 | 15.000 | 29.000 | — |
| | 3 | 8.000 | 16.000 | 26.000 | — |
| | 4 | 9.000 | 12.000 | 26.000 | — |
| | 5 | 8.000 | 15.000 | 26.000 | — |
| Count (n) | | 25 | 25 | 25 | 20 |
| Mean | | 6.640 | 12.440 | 24.400 | 6.944 |
| SD | | 1.524 | 1.938 | 3.240 | 0.555 |
| CV | | 23.1% | 15.6% | 12.9% | 8.3% |

Example 6: Reportable Range and Linearity

Figure 8:
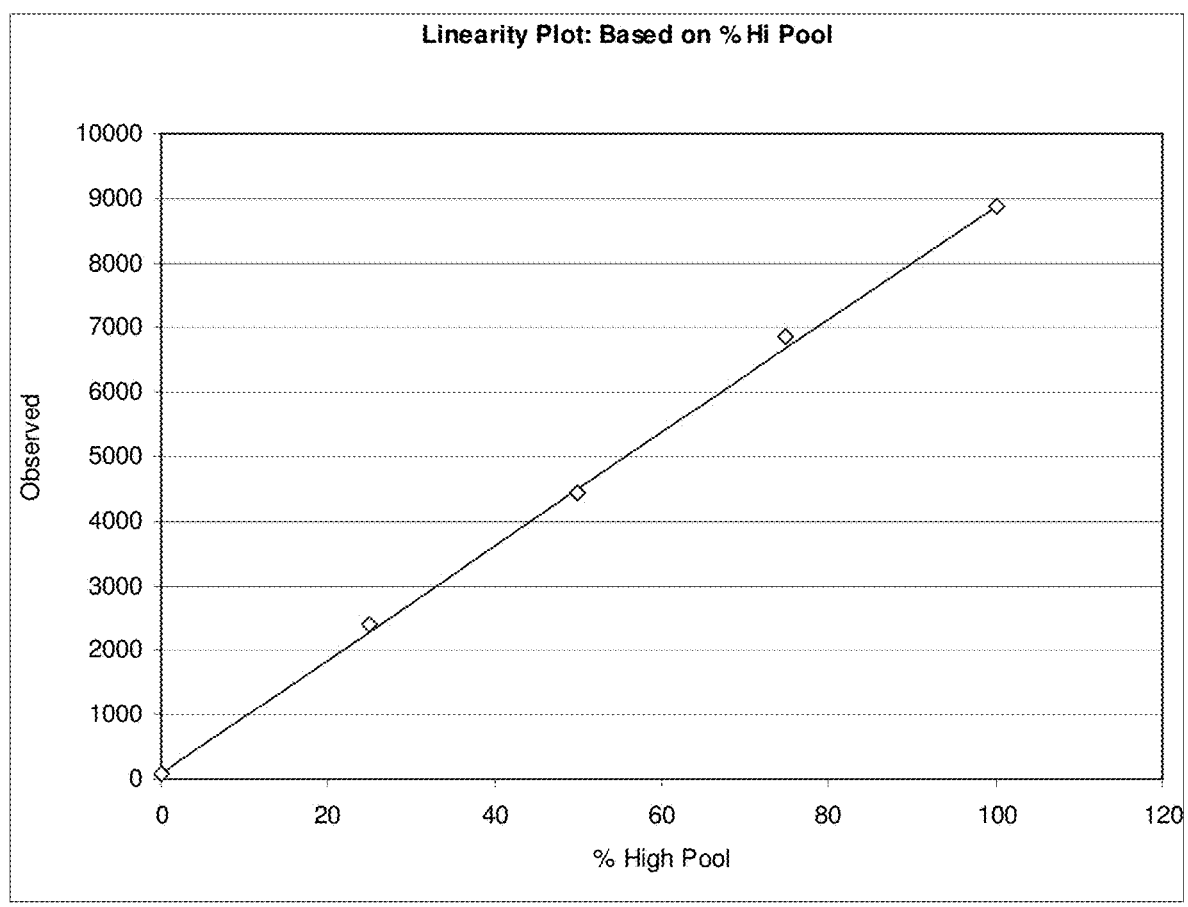
FIG. 8 shows a plot demonstrating the linearity of response for quantitation of TBDMS-MMA in serum measured by monitoring the m/z transition at 289→189 (at 3 V). Details are discussed in Example 6.

A sample with high concentration of MMA (8868 nMol/L) was mixed with a sample with a low concentration of MMA (99 nMol/L) in different proportions to achieve five samples with concentrations across the range. The five samples were prepared with the following proportions 100% Low (expected concentration of 99 nMol/L), 75% Low/25% High (expected concentration of 2291 nMol/L), 50% Low/50% High (expected concentration of 4484 nMol/L), 25% Low/75% High (expected concentration of 6676 nMol/L), and 100% High (expected concentration of 8868 nMol/L). Analysis of samples at these five concentrations as described in Example 4 demonstrated linear response across a reportable range of up to at least about 8870 nMol/L. A graphical representation demonstrating the linearity of response is shown in FIG. 8.

Example 7: Recovery Studies

Six patient serum pools (STD 1-6) were spiked with a known amount of MMA. Samples 1-3 (500 μL) were spiked with 50 μL of 3333 nMol/L MMA standard in stripped serum, and samples 4-6 (500 μL) were spiked with 50 μL of 10,000 nMol/L MMA standard in stripped serum. Non-spiked samples were prepared for comparison by adding 50 μL of blank stripped serum to 500 μL of each of Samples 1-6. For each serum pool, 2 baseline (blank serum added) and 4 spiked replicates were tested as described in Example 4. The amount recovered was calculated as the difference between the mean of the spiked and baseline samples. Percent recovery was calculated to be the ratio of the amount recovered (observed) divided by the amount added. The six pools yielded an average accuracy of about 104.1%. All assays were within the acceptable accuracy range of 85-115%. The results of the spiked specimen recovery studies are presented in Table 6.

TABLE 6

Spiked Specimen Recovery Studies

| | STD 1 | STD 2 | STD 3 | STD 4 | STD 5 | STD 6 |
|---|---|---|---|---|---|---|
| | Measured Concentration (nMol/L) | | | | | |
| Blank | 399.77 | 420.96 | 431.60 | 1070.50 | 1113.17 | 1478.64 |
| Result 1 | 421.41 | 433.23 | 463.68 | 1111.00 | 1169.87 | 1689.27 |
| Result 2 | 434.17 | 440.31 | 449.28 | 1142.52 | 1160.13 | 1533.30 |

TABLE 6-continued

Spiked Specimen Recovery Studies

| | STD 1 | STD 2 | STD 3 | STD 4 | STD 5 | STD 6 |
|---|---|---|---|---|---|---|
| | | | Measured Concentration (nMol/L) | | | |
| Blank | 399.77 | 420.96 | 431.60 | 1070.50 | 1113.17 | 1478.64 |
| Result 3 | 420.86 | 445.55 | 461.15 | 1158.69 | 1193.30 | 1576.17 |
| Result 4 | 414.25 | 422.68 | 429.29 | 1107.55 | 1132.14 | 1555.99 |
| Spiked Mean | 418.09 | 432.55 | 447.00 | 1118.05 | 1153.72 | 1566.67 |
| % Recovery | 104.58 | 102.75 | 103.57 | 104.44 | 103.64 | 105.95 |

Example 8: Method Comparison Studies

Figure 9A:
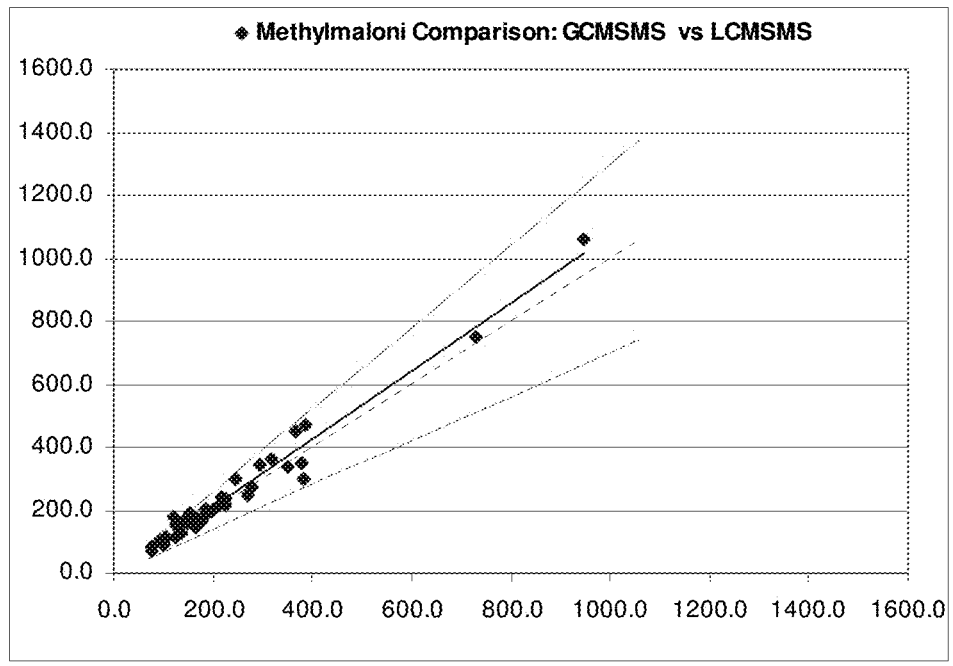
FIGS. 9A and 9B show plots for method comparison between GC-MS/MS and LC-MS/MS.
Figure 9B:
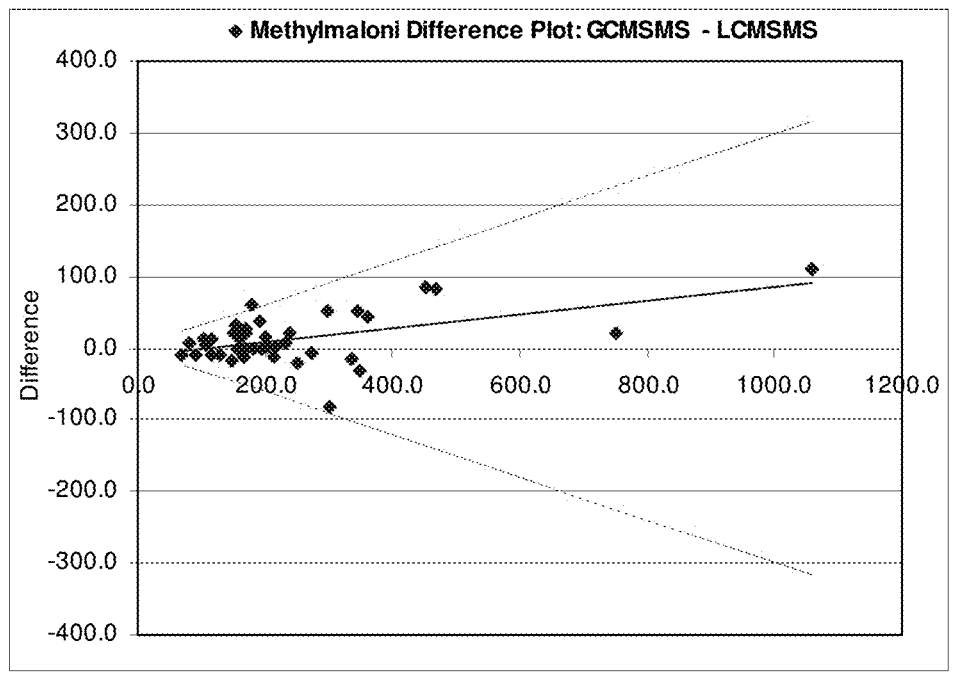

The performance of the GC-MS/MS assay described in Example 4 was compared against quantitation of MMA by LC-MS/MS. Forty patient serum samples were analyzed in four individual runs over four days by each method. Difference and % difference were calculated for each patient sample. The results of these studies are shown plotted in FIG. 9A (GC-MS/MS vs LC-MS/MS) and 9B (difference vs amount detected).

Example 9: Hemolysis, Lipemia, and Icteria Studies

The effect hemolysis, lipemia, and icteria have on the assay was also investigated.

Hemolysis. The effect of hemolysis was evaluated by preparing five patient serum pools as follows. A hemolysate was prepared by washing 2 mL of heparinized whole blood three times with phosphate buffered saline (PBS). After the final wash, the cells were frozen at about −70° C. for about 30 minutes. The hemolyzed cell mixture was removed from the freezer and mixed by mechanical vortex. For each of the five patient serum pools, 200 μL of hemolysate was added to 2 mL of serum. A baseline (non-hemolytic) sample was prepared for each pool by the addition of 200 μL of PBS to 2 mL of serum. For each pool, baseline and hemolytic samples were analyzed in quadruplicate and the differences between mean and hemolyzed samples observed. Results of analysis of all pools were acceptable (i.e., between 85% and 115% of baseline). Results of these studies are presented in Table 7.

Lipemia. The effect of lipemia was evaluated by preparing five patient serum pools each with 200 μL of Intralipid added to 2 mL of serum. A baseline (non-lipemic) sample was prepared for each pool by the addition of 200 μL of PBS to 2 mL of serum. For each pool, baseline and lipemic samples were analyzed in quadruplicate and the differences between mean and lipemic samples observed. Results of analysis of all pools were acceptable (i.e., between 85% and 115% of baseline). Results of these studies are presented in Table 7.

Icteria. The effect of icteria was evaluated by preparing five patient serum pools each with 200 μL of Verichem High Bilirubin Standard Level F (30 mg/dL total and direct bilirubin) added to 2 mL of serum. A baseline (non-icteric) sample was prepared for each pool by the addition of 200 μL of PBS to 2 mL of serum. For each pool, baseline and icteric samples were analyzed in quadruplicate and the differences between mean and icteric samples observed. Results of analysis of four of the five pools were unacceptable (i.e., above 115% of baseline). Results of these studies are presented in Table 7.

TABLE 7

Hemolysis, Lipemia, and Bilirubin Interference Studies

| | Pool 1 | Pool 2 | Pool 3 | Pool 4 | Pool 5 |
|---|---|---|---|---|---|
| Average MMA Concentration (nMol/L) | | | | | |
| Baseline | 210 | 187 | 170 | 199 | 150 |
| Hemolysis | 209 | 193 | 174 | 204 | 157 |
| Icterus | 203 | 188 | 174 | 198 | 152 |
| Lipemia | 223 | 235 | 219 | 238 | 195 |
| % Recovery | | | | | |
| Hemolysis | 100% | 103% | 102% | 103% | 105% |
| Icterus | 97% | 97% | 100% | 97% | 97% |
| Lipemia | 110% | 125% | 126% | 120% | 128% |

Example 7: MMA Reference Intervals

Serum samples from 30 healthy male and 30 healthy female donors (total n=60) were assayed for MMA as described above, and results statistically analyzed to determine reference ranges for healthy individuals. Healthy reference ranges were determined to be within about 67 nMol/L to about 223 nMol/L. No sex difference was observed. Raw data from these studies is presented in Table 8.

TABLE 8

Reference Interval Studies

| Sample | MMA (nMol/L) | Below RI | Above RI |
|---|---|---|---|
| 1 | 137.00 | | |
| 2 | 166.00 | | |
| 3 | 67.00 | | |
| 4 | 100.00 | | |
| 5 | 153.00 | | |
| 6 | 80.00 | | |
| 7 | 136.00 | | |
| 8 | 71.00 | | |
| 9 | 61.00 | YES | |
| 10 | 111.00 | | |
| 11 | 96.00 | | |
| 12 | 129.00 | | |
| 13 | 101.00 | | |
| 14 | 161.00 | | |
| 15 | 95.00 | | |
| 16 | 197.00 | | |
| 17 | 169.00 | | |
| 18 | 203.00 | | |
| 19 | 121.00 | | |
| 20 | 113.00 | | |
| 21 | 125.00 | | |
| 22 | 126.00 | | |
| 23 | 277.00 | | YES |
| 24 | 122.00 | | |
| 25 | 124.00 | | |
| 26 | 160.00 | | |
| 27 | 84.00 | | |
| 28 | 144.00 | | |
| 29 | 120.00 | | |
| 30 | 104.00 | | |
| 31 | 96.00 | | |
| 32 | 98.00 | | |
| 33 | 99.00 | | |
| 34 | 109.00 | | |
| 35 | 163.00 | | |
| 36 | 106.00 | | |
| 37 | 156.00 | | |
| 38 | 111.00 | | |
| 39 | 120.00 | | |

TABLE 8-continued

Reference Interval Studies

| Sample | MMA (nMol/L) | Below RI | Above RI |
|---|---|---|---|
| 40 | 143.00 | | |
| 41 | 134.00 | | |
| 42 | 159.00 | | |
| 43 | 76.00 | | |
| 44 | 101.00 | | |
| 45 | 230.00 | | YES |
| RI Lower Limit | 67 | | |
| RI Upper Limit | 223 | | |
| Number of donors | 45 | | |
| Number above RI | 2 | | |
| Percent above RI | 4.4% | | |
| Number below RI | 1 | | |
| Percent below RI | 2.2% | | |
| Percent outside RI | 6.7% | | |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of methylmalonic acid in a sample by tandem mass spectrometry, the method comprising:
    (a) adding a deuterated internal standard to a first sample containing methylmalonic acid to form a second sample;
    (b) purifying the second sample by solid phase extraction;
    (c) subjecting the purified sample from step (b) to a derivatizing agent under conditions suitable to generate a derivatized methylmalonic acid;
    (d) subjecting the derivatized methylmalonic acid to liquid chromatography;
    (e) ionizing the derivatized methylmalonic acid by electron impact ionization to generate a precursor ion and fragmenting the precursor ion using collision energy of 3 V or 10 V to generate one or more fragment ions; and
    (f) determining the amount of said one or more fragment ions by tandem mass spectrometry;
    wherein the amount of said one or more fragment ions determined in step (f) is related to the amount of methylmalonic acid originally present in the sample, wherein the method is capable of detecting about 9 nMol/L of methylmalonic acid, and wherein the derivatized methylmalonic acid is a tert-butyldimethylsilyl derivatized methylmalonic acid.

2. The method of claim 1, wherein said sample comprises plasma or serum.

3. The method of claim 1, wherein said one or more fragment ions comprise an ion with m/z of $189.0 \pm 0.5$.

4. The method of claim 1, wherein said one or more fragment ions comprise an ion with m/z of $147.0 \pm 0.5$.

5. The method of claim 1, wherein said one or more fragment ions comprise an ion with m/z of $189.0 \pm 0.5$ and an ion with m/z of $147.0 \pm 0.5$.

* * * * *